(12) United States Patent
Kolossov et al.

(10) Patent No.: US 9,321,997 B2
(45) Date of Patent: Apr. 26, 2016

(54) TISSUE MODELING IN EMBRYONIC STEM (ES) CELL SYSTEM

(75) Inventors: Eugen Kolossov, Köln (DE); Jürgen Hescheler, Köln (DE); Heribert Bohlen, Köln (DE); Bernd Fleischmann, Bonn (DE); Wilhelm Röll, Bonn (DE); Andreas Ehlich, Mechernich (DE); Jessica Königsmann, Berlin (DE)

(73) Assignee: AXIOGENESIS AG, Cologne (DE)

( * ) Notice: Subject to any disclaimer, the term of this patent is extended or adjusted under 35 U.S.C. 154(b) by 1786 days.

(21) Appl. No.: 10/561,780

(22) PCT Filed: Jun. 21, 2004

(86) PCT No.: PCT/EP2004/006698
§ 371 (c)(1),
(2), (4) Date: Jul. 2, 2007

(87) PCT Pub. No.: WO2004/113515
PCT Pub. Date: Dec. 29, 2004

(65) Prior Publication Data
US 2007/0258948 A1    Nov. 8, 2007

Related U.S. Application Data

(60) Provisional application No. 60/480,212, filed on Jun. 20, 2003.

(30) Foreign Application Priority Data

Jun. 20, 2003 (EP) ..................... 03013980

(51) Int. Cl.
| | |
|---|---|
| C12N 5/00 | (2006.01) |
| C12N 5/071 | (2010.01) |
| C12N 5/077 | (2010.01) |
| A61K 35/33 | (2015.01) |
| A61K 35/34 | (2015.01) |
| A61K 35/44 | (2015.01) |
| C12Q 1/68 | (2006.01) |
| G01N 33/50 | (2006.01) |

(52) U.S. Cl.
CPC .............. *C12N 5/0697* (2013.01); *A61K 35/33* (2013.01); *A61K 35/34* (2013.01); *A61K 35/44* (2013.01); *C12N 5/0657* (2013.01); *C12N 2502/13* (2013.01); *C12N 2502/28* (2013.01); *C12N 2506/02* (2013.01); *C12N 2510/00* (2013.01); *C12Q 1/6881* (2013.01); *C12Q 1/6897* (2013.01); *G01N 33/5088* (2013.01); *G01N 2800/52* (2013.01)

(58) Field of Classification Search
CPC .... C12N 5/0697; C12N 5/0657; A61K 35/44; A61K 35/33
See application file for complete search history.

(56) References Cited

U.S. PATENT DOCUMENTS

| | | | |
|---|---|---|---|
| 5,733,727 A | 3/1998 | Field | |
| 5,928,943 A * | 7/1999 | Franz et al. | 435/363 |
| 6,458,589 B1 * | 10/2002 | Rambhatla et al. | 435/370 |
| 7,105,344 B2 | 9/2006 | Hescheler | |
| 7,449,306 B2 * | 11/2008 | Elson et al. | 435/40.52 |
| 7,452,718 B2 * | 11/2008 | Gold et al. | 435/377 |
| 2002/0022268 A1 * | 2/2002 | Xu et al. | 435/366 |
| 2004/0096432 A1 | 5/2004 | Fleischmann et al. | |
| 2006/0168665 A1 | 7/2006 | Hescheler | |
| 2007/0014772 A1 * | 1/2007 | Cohen et al. | 424/93.7 |
| 2008/0019952 A1 | 1/2008 | Kolossov et al. | |

FOREIGN PATENT DOCUMENTS

| | | |
|---|---|---|
| WO | WO 98/49333 | 11/1998 |
| WO | WO 99/09152 | 2/1999 |
| WO | WO 00/63221 | 10/2000 |
| WO | WO 02/051987 A1 | 7/2002 |
| WO | WO 03/010303 A1 | 2/2003 |
| WO | WO 03/018760 A2 | 3/2003 |

OTHER PUBLICATIONS

Wantanabe et al. Biochem Biophys Res Com 213(1):130-137, 1995.*
Feld et al. Circulation 105:522-529, Jan. 2002.*
Itskovitz-Eldor et al. Molecular Medicine 6(2):88-95, 2000.*
Mandel et al. Journal of Clinical Investigation 51:1378-1387, 1972.*
Kettenhofen, R., et al., "Transgenic Murine Embryonic Stem Cells as an *in vitro* Model for Developmental Toxicity—An Alternative to the Gold Standard," *Naunyn-Schmiedeberg's Arch. Pharmacol 365, Suppl. 1*:R154, Springer Verlag, Abstract No. 601 (Mar. 2002).
Kolossov, E., et al., "Transplantation of the Cardiomyocytes Selected from Transgenically Designed ES cells: Quality Control and Engrafting Support of Fibroblasts," *Tissue Engineering 9*:853-854, Mary Ann Liebert, Inc., Abstract No. 230 (Aug. 2003).
Mummery, C., et al., "Differentiation of Human Embryonic Stem Cells to Cardiomyocytes: Role of Coculture With Visceral Endoderm-Like Cells," *Circulation 107*:2733-2740, Lippincott Williams and Wilkins (Jun. 2003).
Müller, M., et al., "Selection of ventricular-like cardiomyocytes from ES cells *in vitro*," *FASEB J. 14*:2540-2548, The Federation of American Societies for Experimental Biology (2000).
Sachinidis, A., et al., "Cardiac specific differentiation of mouse embryonic stem cells," *Cardiovascular Research 58*:278-291, Elsevier Science B.V. (May 2003).

(Continued)

*Primary Examiner* — Marcia S Noble
(74) *Attorney, Agent, or Firm* — Fanelli Haag PLLC

(57) ABSTRACT

Provided are embryonic stem (ES) cell-derived tissue modeling systems. In particular, systems for the de novo generation of tissue by parallel drug selection of cell types constituting the tissue of interest in one culture of differentiating ES cells is described as well as the use of such systems in transplantation and drug development.

21 Claims, 9 Drawing Sheets

(56) References Cited

OTHER PUBLICATIONS

Spielmann, H., et al., "The use of transgenic embryonic stem (ES) cells and molecular markers of differentiation for improving the embryonic stem cell test (EST)," *Congenit. Anom. 40*:S8-S18, Japanese Teratology Society (2000).
International Search Report for International Application No. PCT/EP2004/006698, mailed on Feb. 1, 2005, European Patent Office, Netherlands.
U.S. Appl. No. 10/594,177 (U.S. National Phase of PCT/EP04/07529), inventors Ehlich, et al., I.A. filed Jul. 8, 2004 (Not Yet Published).
U.S. Appl. No. 11/547,871 (U.S. National Phase of PCT/EP05/03662), inventors Bohlen, et al., I.A. filed Apr. 7, 2005 (Not Yet Published).
U.S. Appl. No. 11/596,262 (U.S. National Phase of PCT/EP05/05087), inventors Bohlen, et al., I.A. filed May 11, 2005 (Not Yet Published).
English translation of JP 2002-051782.
English translation of the JP Office Action, JP Appl. No. 2011-18577.
Communication of Dec. 6, 2010 from EPO in EP 04 737 076.2.
Communication of Sep. 24, 2012 from EPO in EP 04 737 076.2.
Communication of Mar. 12, 2013 from EPO in EP 04 737 076.2.
Communication of Jun. 19, 2014 from EPO in EP 04 737 076.2.
Communication of Mar. 7, 2013 from EPO in EP 12 197 213.7.
Communication of Jun. 17, 2014 from EPO in EP 12 197 213.7.
Communication of Nov. 13, 2015 from EPO in EP 12 197 213.7.
Rajabalian, S., et al., "Supportive Effects of Human Embryonic Fibroblast Cell Lines on Growth and Proliferation of EBV-Transformed Lymphoblastoid Cells," *Iranian Biomedical Journal* 7(4):147-153 (2003).
Shamblott, M.J. et al., "Derivation of Pluripotent Stem Cells from Cultured Human Primordial Germ Cells," *Proc. Natl. Acad. Sci.* 95:13726-13731 (1998).
Klimanskaya, I., et al., "Human Embryonic Stem Cell Lines Derived from Single Blastomere," *Nature* 444: 1-5 (2006).
Gepstein, L, "Derivation and Potential Applications of Human Embryonic Stem Cells," *Circulation Research* 91:866-876 (2002).
Amit, M., et al., "Human Feeder Layers for Human Embryonic Stem Cells," *Biology of Reproduction* 68:2150-2156 (2003).
Chung, Y. et al., "Human Embryonic Stem Cell Lines Generated without Embryo Destruction," *Cell Stem Cell* 2:1-5 (2008).
Glossary. In *Stem Cell information*. National Institutes of Health, U.S. Department of Health and Human Services, 2014.
Young, H.E. And Black, A.C., "Adult Stem Cells," *The Anatomical Record Part A* 276A: 75-102 (2004).
Zhao, Y. et al., "A Human Peripheral Blood Monocyte-Derived Subset Acts as Pluripotent Stem Cells," *PNAS* 100(5):2426-2431 (2003).
Jiang, Y. et al., "Pluripotency of Mesenchymal Stem Cells Derived from Adult Marrow," *Nature* 418:41-49 (2002).
Gumpel, M. et al., "Transplantation of Human Ebryonic Oligodendrocytes into Shiverer Brain," *Annal New York Academy of Sciences* 495:70-85 (1987).
Kikuchi, K., et al., "Roles of Embryonic Astrocytes and Schwann Cells in Regeneration of Adult Rat Dorsal Root Axons: Qualitative Observations," *Neurol. Med. Chir.* 33: 682-690 (1993).

* cited by examiner

TISSUE MODELING IN EMBRYONIC STEM (ES) CELL SYSTEM

CROSS-REFERENCE TO RELATED APPLICATIONS

This application is a U.S. National Phase of PCT/EP04/06698, filed Jun. 21, 2004 which claims benefit of U.S. Provisional Application No. 60/480,212, filed Jun. 20, 2003, and European Patent Application No. 03013980.2, filed Jun. 20, 2003, each of which is hereby incorporated by reference in its entirety.

FIELD OF THE INVENTION

The present invention is concerned generally with the use of embryonic and embryonic stem cell-derived cell types suitable for use in tissue regeneration, and non-therapeutic applications such as drug screening.

BACKGROUND ART

Precursor cells have become a central interest in medical research. Many tissues in the body have a back-up reservoir of precursors that can replace cells that are senescent or damaged by injury or disease. Considerable effort has been made recently to isolate precursors of a number of different tissues for use in regenerative medicine. Sources and systems for producing differentiated cells from a stem cell population for use wherever a relatively homogenous cell population is desirable have been summarized in for example U.S. patent application US2003/0040111. Multi- and pluripotent embryonic stem (ES) cells as well as embryonic germ (EG) cells of mammals can be induced to differentiate in culture into a variety of cell types, including cardiac muscle cells. However, ES cell-derived cardiomyocytes constitute only 1% to 5% of all cells in differentiated embryoid bodies (EBs). The large fraction of it is comprised of undifferentiated ES cells bearing significant tumorogenic potential.

Recently, genetic selection of specified cell types from differentiating cultures of embryonic stem (ES) cells based on the use of tissue-specific gene-regulatory elements—promoters driving a drug resistance cassette has been described; see, e.g., international application WO02/051987. Thus, the certain differentiated cell types originated from transgenic ES clones possessing the corresponding vector, could be selected by applying the corresponding drug that eliminates all other emerging cell types as well as undifferentiated ES cells. Up to date this approach has been proven as most specific and efficient for a high grade of purification of cardiac, neuronal and insulin-secreting cells from cultures of differentiating ES cells.

Nevertheless, a significant challenge to the use of stem cells for therapy is to control growth and differentiation into the particular type of tissue required for the treatment of each patient. Thus, there is a need for new approaches to generate populations of differentiated cells and tissues suitable for human administration. The solution to said technical problem is achieved by providing the embodiments characterized in the claims, and described further below.

SUMMARY OF THE INVENTION

It is known that every tissue consists of a main specific cell type which determines its functional role along with supporting cell types (e.g. fibroblasts, stromal, endothelial, glial cells, etc.), which are important for maintaining of the three-dimensional architectonic structure of a tissue, its trophic function and interconnections with other tissue systems of the whole organism.

The present invention is based on the theory that layout of most of the tissues constituting an adult organism is established in the early embryonic development when the corresponding cell types appear during differentiation forming interconnections in accordance with specific signaling molecules and emerging receptors. Thus, one can expect that when different cell types contributing to a certain tissue type are genetically selected from the same culture of differentiating ES cells, they should form interconnections and architectonics according to their natural, genetically determined specific clues. In such case, the high level of purification of the cells of interest in one differentiating culture of genetically modified ES cells is the main premise for "self-assembling" of a tissue-like structure in the course of differentiation of ES cells in vitro.

In accordance with the present invention it could be surprisingly shown that co-culturing and co-transplantation of ES cell-derived cardiomyocytes with embryonic fibroblasts lead to cardiac tissue-like formation in vitro and significantly improves transplantation results when injected to the cryoinfarcted hearts of mice.

Thus, in one aspect the present invention relates to a method of modeling and/or obtaining tissue or tissue-like structures comprising culturing an embryonic stem (ES) cell-derived first cell type in the presence of at least one embryonic second cell type; and allowing integration and alignment of said at least two cell types into tissue or tissue-like structures, wherein preferably the ES cell of said ES cell-derived first cell type comprises a selectable marker operably linked to a first cell type-specific regulatory sequence specific for said first cell type. Hence, the application of a high-efficiency system of drug selection effectively increases (5 to 10 times) the final yield due to the intensive cardiomyocytes proliferation and reduces the threat of tumor development after transplantation to a negligible level.

In accordance with the above, the present invention generally relates to a method of improving tissue repair and/or organ function in a mammal comprising the steps of:
(a) introducing a cellular inoculum comprising a co-culture of ES cell-derived cell types in which differentiation has been initiated with embryonic supporting cells or introducing a differentiated tissue to at least a portion of the previously damaged area of the tissue; and
(b) allowing said introduced cellular inoculum to engraft in situ as viable cells or tissue situated within the previously damaged area of the tissue, wherein the engraftment results in an improved tissue and/or organ function in said mammal.

The supporting cells are preferably fibroblasts and/or endothelial cells.

In particular, a method for improving the cardiac function in a mammal after a myocardial infarct is provided, said method comprising the steps of:
(a) culturing undifferentiated mammalian embryonic stem (ES) cells comprising a resistance gene and a reporter gene under the control of the same cardiac-specific promoter in vitro in a culture medium containing the selective agent for the resistance gene under conditions allowing differentiation of said ES cells into cardiomyocytes;
(b) isolating said differentiated cardiomyocytes and/or eliminating non-differentiated cells, optionally along with cells differentiating towards irrelevant cell types from said cardiomyocytes in the course of differentiation;

(c) subsequently co-transplanting said cardiomyocytes with embryonic or ES cell-derived fibroblasts and or endothelial cells to at least a portion of the previously infarcted area of the heart tissue; and (d) allowing said introduced cellular inoculum to engraft in situ as viable cells situated within the previously infarcted area of the heart tissue, wherein the engraftment results in an improved cardiac function in said mammal.

For the actual transplantation, it is to be understood that co-transplanting of the cells may not be done concomitantly but also subsequently in either way.

It might be that not always embryonic cells are available as a source for supporting the ES cell-derived cell type to develop into a certain tissue or that the given embryonic cells are not suitable for this purpose. Furthermore, other reasons may exist why the use of those cells is not appropriate, for example because of the different developmental status of the cells.

In order to overcome those potential obstacles it has been contemplated in accordance with the invention to provide the additional cell types from ES cells as well.

Thus, a ES cell-derived tissue-modeling system has been developed. The core of the proposed approach is a parallel drug selection of cell types constituting tissues of interest in one culture of differentiating ES cells. One advantage of such approach is that interactions between purified cell types are processed in a "natural" way immediately upon releasing from irrelevant cells, using natural clues for "cross-talk" signaling and forming viable tissue-like structures as an outcome. In accordance with the present invention, in principle two variants of such an approach can be used:

a) multiple transgenic ES clones are stably transfected with a certain number of vectors with a drug selection cassette driven by specific promoters according to the cell types constituting the desirable tissue type. In such a variant all emerging cell types have origin from one common ES cell clone predecessor and the resulting ratio between different cell components depends on the relative differentiation rate of each of them; see FIGS. 2A and 3B.

b) chimeric embryoid bodies (EBs) are used by which approach a number of transgenic ES clones is generated, where each single clone possesses only one vector with a drug resistance cassette driven by one of the cell type-specific promoters. For tissue modeling the relevant clones should be mixed at the initial phase of differentiation ("hanging drops" or "mass culture") in order to form ES cell aggregates (EBs) where, after drug selection, emerging cell types have origin from different corresponding ES cell clones and the final ratio of the cell components also depends on and can be controlled by the initial ratio between different ES cell lines; see FIGS. 2B and 3C.

Thus, in further aspect the present invention relates to a method of modeling and/or obtaining tissue or tissue-like structures comprising the following steps:

(a) transfecting one or more multi- or pluripotent cells with recombinant nucleic acid molecules comprising a first and a second cell type-specific regulatory sequence operably linked to at least one selectable marker, wherein said second cell type is different from said first cell type;

(b) culturing the cells under conditions allowing differentiation of the cells; and (c) isolating cells of at least two differentiated cell types and/or eliminating non-differentiated cells, optionally along with cells differentiating towards irrelevant cell types from the cell types of interest that activate the selectable marker in the course of differentiation.

Also in this method embryonic stem (ES) cells are preferred, however embryonic germ (EG) cells may be used as well. Likewise, the present invention relates to cells obtainable by the methods of the invention, wherein said cells are capable of differentiating into at least two cell types. Likewise, a cell aggregate of at least two different cell types obtainable by the method of the invention and tissue comprising cells or a cell aggregate as obtainable by the method of the invention are encompassed as well as organs, implants and transplants comprising those cells, cell aggregates or tissue.

The prospect of using human ES cells in the tissue replacement therapy makes the problem of high level purification of the ES cell-derived differentiated cell types as one of the cornerstones of the future ES cell-based transplantology. The high standards and criteria of purity for ES cell-derived specific cell types selected for therapeutic purposes have still to be established. Up to date, on murine model, the approach based on drug selection of differentiated cell types derived from genetically modified ES cells has proven to be the most effective one in terms of absence of undifferentiated ES cells in the final yield as well as low incidence rate of embryonic carcinomas in recipient animals. Beside the issue of purity, the quality of the grafting of transplanted cells into the recipient tissue, particularly an impaired one, could heavily depend on supporting cells (connecting fibroblasts, stromal, endothelial, glial cells, etc.). All these important tissue elements suffer in damaged tissue of recipient as well as the main cell type, and by this create additional problems for the process of grafting of the transplanted cells, especially on its earliest steps. Thus, tissue modeling during human ES cell differentiation could become a relevant method of obtaining of a viable tissue prototype with high feasibility for transplantation.

Accordingly, the present invention also relates to methods of treatment of damaged tissue or organs in a subject comprising implanting or transplanting to the subject in need thereof cells, cell aggregates, tissue or an organ obtained by the methods of the present invention. In a particular aspect, the present invention relates to a method for improving the cardiac function in a mammal after a myocardial infarct, said method comprising the steps of:

(a) transfecting mammalian embryonic stem (ES) cells with a recombinant nucleic acid molecule comprising a resistance gene under the control of cardiac, fibroblast and optionally endothelium-specific regulatory sequences, and optionally comprising one or more reporters under the same specific regulatory sequences;

(b) culturing said ES cells in vitro in a culture medium containing the selective agent for the resistance gene under conditions allowing differentiation of said ES cells into cardiomyocytes, fibroblasts and optionally endothelial cells;

(c) eliminating from said differentiated cardiomyocytes, fibroblasts and optionally endothelial cells non-differentiated cells, optionally along with cells differentiating towards irrelevant cell types; optionally (d) allowing aligning of said differentiating cardiomyocytes, fibroblasts and optionally endothelial cells into cardiac-like tissue;

(e) subsequently co-transplanting said cardiomyocytes, fibroblasts and optionally endothelial cells or said tissue to at least a portion of the previously infarcted area of the heart tissue; and (f) allowing said introduced cells or tissue to engraft in situ as viable cells situated within the previously infarcted area of the heart tissue, wherein the engraftment results in improved cardiac function in said mammal.

Vectors and compositions of vectors comprising the recombinant nucleic acid molecules as used in the methods of the present invention are also subject of the present invention, so are cells comprising such a vector or vector compositions.

In vitro-modeling of different types of tissue from, e.g., murine ES cells has different applications in (i) in vitro studies on early steps of tissue formation during embryonic development as well as on the influence of different kinds of factors and chemicals on this process. The latter makes the proposed approach valuable for (ii) in vitro high throughput embryotoxicology assay, where a variety of substances can be tested not only for their ability to influence the cell type specific differentiation but, also the intimate the process of "self-assembling" of differentiated cells in a specialized tissue type. Formation of such tissue-like structures in vitro assumes also their improved functionality and viability compared to singled counterparts. Thus, the methods of the present invention provide a good basis for (iii) in vitro high throughput pharmacological and pharmakinetic assays, where different compounds with expected tissue targeting effects could be tested for their direct functional and side effects on tissue level. All above-mentioned implications assume significant decrease of the expensive and ethically controversial animals consumption for both scientific and screening purposes. All above mentioned items for murine ES cells ((i), (ii), (iii)) are completely applicable to the tissue modeling from human ES cells with remarkable accent on those as practically only possible choice for providing embryological studies and high throughput screening on a human model.

For such embodiments, the use of chips or arrays containing the differentiating cells of the present invention are particularly suited. Hence, the present invention also relates to arrays comprising a solid support and attached thereto or suspended thereon cells, a cell aggregate or tissue prepared in accordance with the present invention, in particular microelectrode arrays (MEAs) are concerned. In this context, devices adapted for analyzing such arrays are encompassed by the present invention as well.

Hence, the instant invention also relates to methods for obtaining and/or profiling a test substance capable of influencing cell development and/or tissue structure formation comprising the steps:

(a) contacting a test sample comprising cells, a cell aggregate, tissue or an organ prepared in accordance with the present invention with a test substance; and (b) determining a phenotypic response in said test sample compared to a control sample, wherein a change in the phenotypic response in said test sample compared to the control sample is an indication that said test substance has an effect on cell development and/or tissue structure formation.

Those methods, which are preferably performed on a chip or array, are advantageously implemented in any one of the methods for obtaining/modeling tissue described herein, wherein said test sample is contacted with said test substance prior to, during or after said cell or cell aggregate passed through said method. These screening methods can be combined with or refined to methods of manufacturing drugs, in particular of drugs which support wound healing and/or healing of damaged tissue. Those methods may comprise for example mixing the substance isolated with a pharmaceutically acceptable carrier and packaging into an appropriate container with corresponding prescriptions for the envisaged therapeutic treatment.

For all the methods of the present invention described kits are provided useful for conducting those methods and containing the mentioned vectors or compositions of vectors, arrays, multi- or pluripotent cells, and optionally a culture medium, recombinant nucleic acid molecules, standard compounds, etc.

Other embodiments of the invention will be apparent from the description that follows.

DESCRIPTION OF THE INVENTION

Figure 1:
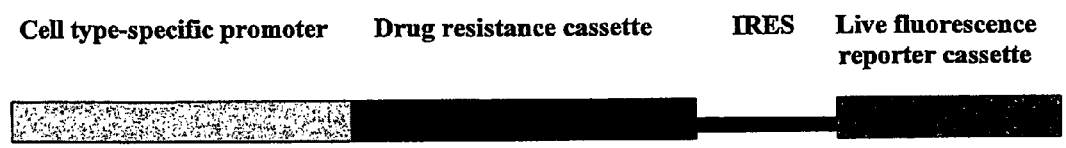
FIG. 1: Principal scheme of the vectors for tissue modeling in the ES cells system of the present invention.

Stem cells of various kinds have become an extremely attractive modality in regenerative medicine. They can be proliferated in culture, and then differentiated in vitro or in situ into the cell types needed for therapy. Without intending to be bound by theory, it is a hypothesis of this invention that some of the populations of differentiated cells produced using adaptive culture and positive selection methods will be sub-optimal for use in human therapy. In some circumstances, undifferentiated cells in the population may impair engraftment or function of the cells in vivo. Undifferentiated cells may also increase the possibility of a malignancy or other tumor forming at the site of the therapeutic implant, or by migration of transplanted cells. In addition or alternatively, the provision and engraftment of one particular embryonic cell type may often not be sufficient to achieve reconstitution of, for example, damaged tissue.

This invention is directed towards methods of providing protocols and methods for providing de novo tissue and organs particularly useful for transplantation and other purposes. In a first set of experiments in accordance with the present invention it could be shown that puromycin-purified cardiomyocytes show integration and alignment with embryonic fibroblasts in co-culture into tissue-like structures. The question however remained whether those tissue-like structures are comparable with or at least close enough to native cardiac tissue and, if so, whether the effect observed under in vitro culture can also be achieved in vivo.

Further experiments could demonstrate that puromycin-selected ES cell-derived cardiomyocytes indeed can be successfully engrafted in the cryo-infarcted areas at the heart of a mouse when co-transplanted with syngenic embryonic fibroblasts. Those ES cell-derived cardiomyocytes display morphology of different cardiac subtypes featuring a well-developed contractile apparatus.

Hence, a high efficiency system of drug selection and quality control of transgenic ES cell-derived cell types such as cardiomyocytes has been established. The drug selection effectively increases (5 to 10 times) the final yield due to the intensive cell type-specific proliferation and reduces the threat of tumor development after transplantation to a negligible level. Moreover, co-culturing or co-transplantation of ES cell-derived cell types with embryonic cell types belonging to connective tissue such as fibroblasts allows the generation of native tissue and tissue-like structures in vitro and in vivo.

The techniques of this invention are designed in part to provide cell populations with improved characteristics for human therapy. After depleting undifferentiated cells, the population of different differentiated embryonic and ES cell-derived cell types is expected to possess better functional and engraftment characteristics, and to have reduced risk of creating unwanted tissue architecture and malignancies in the treated subject. In addition, cell populations of different embryonic and ES cell-derived cell types developing into tissue are more closely related to the in vivo situation, which provides a distinct advantage for non-therapeutic applications such as screening drug candidates.

DEFINITIONS

For the purposes of this description, the term "stem cell" can refer to either stem cell or germ cell, for example embryonic stem (ES) and germ (EG) cell, respectively. Minimally, a stem cell has the ability to proliferate and form cells of more than one different phenotype, and is also capable of self renewal—either as part of the same culture, or when cultured under different conditions. Embryonic stem cells are also typically telomerase-positive and OCT-4 positive. Telomerase activity can be determined using TRAP activity assay (Kim et al., Science 266 (1997), 2011), using a commercially available kit (TRAPeze® XK Telomerase Detection Kit, Cat. s7707; Intergen Co., Purchase N.Y.; or TeloTAGGG™ Telomerase PCR ELISAplus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

In accordance with the present invention, the term embryonic stem (ES) cell includes any multi- or pluripotent stem cell derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice. "Embryonic germ cells" or "EG cells" are cells derived from primordial germ cells. The term "embryonic germ cell" is used to describe cells of the present invention that exhibit an embryonic pluripotent cell phenotype. The terms "human embryonic germ cell (EG)" or "embryonic germ cell" can be used interchangeably herein to describe mammalian, preferably human cells, or cell lines thereof, of the present invention that exhibit a pluripotent embryonic stem cell phenotype as defined herein. Thus, EG cells are capable of differentiation into cells of ectodermal, endodermal, and mesodermal germ layers. EG cells can also be characterized by the presence or absence of markers associated with specific epitope sites identified by the binding of particular antibodies and the absence of certain markers as identified by the lack of binding of certain antibodies.

"Pluripotent" refers to cells that retain the developmental potential to differentiate into a wide range of cell lineages including the germ line. The terms "embryonic stem cell phenotype" and "embryonic stem-like cell" also are used interchangeably herein to describe cells that are undifferentiated and thus are pluripotent cells and that are capable of being visually distinguished from other adult cells of the same animal.

Included in the definition of ES cells are embryonic cells of various types, exemplified by human embryonic stem cells, described by Thomson et al. (Science 282 (1998), 1145); embryonic stem cells from other primates, such as Rhesus stem cells (Thomson et al., Proc. Natl. Acad. Sci. USA 92 (1995), 7844), marmoset stem cells (Thomson et al., Biol. Reprod. 55 (1996), 254) and human embryonic germ (hEG) cells (Shamblott et al., Proc. Natl. Acad. Sci. USA 95 (1998), 13726). Other types of pluripotent cells are also included in the term. Any cells of mammalian origin that are capable of producing progeny that are derivatives of all three germinal layers are included, regardless of whether they were derived from embryonic tissue, fetal tissue, or other sources. The stem cells employed in accordance with the present invention that are preferably (but not always necessary) karyotypically normal. However, it is preferred not to use ES cells that are derived from a malignant source.

"Feeder cells" or "feeders" are terms used to describe cells of one type that are co-cultured with cells of another type, to provide an environment in which the cells of the second type can grow. The feeder cells are optionally from a different species as the cells they are supporting. For example, certain types of ES cells can be supported by primary mouse embryonic fibroblasts, immortalized mouse embryonic fibroblasts (such as murine STO cells, e.g., Martin and Evans, Proc. Natl. Acad. Sci. USA 72 (1975), 1441-1445), or human fibroblast-like cells differentiated from human ES cells, as described later in this disclosure. The term "STO cell" refers to embryonic fibroblast mouse cells such as are commercially available and include those deposited as ATCC CRL 1503.

The term "embryoid bodies" (EBs) is a term of art synonymous with "aggregate bodies". The terms refer to aggregates of differentiated and undifferentiated cells that appear when ES cells overgrow in monolayer cultures, or are maintained in suspension cultures. Embryoid bodies are a mixture of different cell types, typically from several germ layers, distinguishable by morphological criteria; see also infra.

The terms "polynucleotide" and "nucleic acid molecule" refer to a polymer of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. As used in this disclosure, the term polynucleotides refers interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form. Included are nucleic acid analogs such as phosporamidates and thiophosporamidates.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

A "regulatory sequence" or "control sequence" is a nucleotide sequence involved in an interaction of molecules that contributes to the functional regulation of a polynucleotide, such as replication, duplication, transcription, splicing, translation, or degradation of the polynucleotide. Transcriptional control elements include promoters, enhancers, and repressors.

Particular gene sequences referred to as promoters, like the "AMHC" or "collagen" promoter, are polynucleotide sequences derived from the gene referred to that promote transcription of an operatively linked gene expression product. It is recognized that various portions of the upstream and intron untranslated gene sequence may in some instances contribute to promoter activity, and that all or any subset of these portions may be present in the genetically engineered construct referred to. The promoter may be based on the gene sequence of any species having the gene, unless explicitly restricted, and may incorporate any additions, substitutions or deletions desirable, as long as the ability to promote transcription in the target tissue. Genetic constructs designed for treatment of humans typically comprise a segment that is at least 90% identical to a promoter sequence of a human gene. A particular sequence can be tested for activity and specificity, for example, by operatively linking to a reporter gene; see FIG. 1.

Genetic elements are said to be "operatively linked" if they are in a structural relationship permitting them to operate in a manner according to their expected function. For instance, if a promoter helps to initiate transcription of the coding sequence, the coding sequence can be referred to as operatively linked to (or under control of) the promoter. There may be intervening sequences between the promoter and coding region so long as this functional relationship is maintained.

In the context of encoding sequences, promoters, and other genetic elements, the term "heterologous" indicates that the element is derived from a genotypically distinct entity from that of the rest of the entity to which it is being compared. For example, a promoter or gene introduced by genetic engineering techniques into an animal of a different species is said to be a heterologous polynucleotide. An "endogenous" genetic element is an element that is in the same place in the chromosome where it occurs in nature, although other elements may be artificially introduced into a neighboring position.

The terms "polypeptide", "peptide" and "protein" are used interchangeably in this disclosure to refer to polymers of amino acids of any length. The polymer may comprise modified amino acids, it may be linear or branched, and it may be interrupted by non-amino acids.

DETAILED DESCRIPTION OF THE
EMBODIMENTS OF THE PRESENT
INVENTION

In one aspect, the present invention relates to a method of modeling and/or obtaining tissue or tissue-like structures comprising culturing an embryonic stem (ES) cell-derived first cell type in the presence of at least one embryonic second cell type; and allowing integration and alignment of said at least two cell types into tissue or tissue-like structures.

The invention can be practiced using stem cells of any vertebrate species. Included are stem cells from humans; as well as non-human primates, domestic animals, livestock, and other non-human mammals. Amongst the stem cells suitable for use in this invention are primate pluripotent stem cells derived from tissue formed after gestation, such as a blastocyst, or fetal or embryonic tissue taken any time during gestation. Non-limiting examples are primary cultures or established lines of embryonic stem cells. The invention is also applicable to adult stem cells. It is referred to the literature of Anderson et al., Nat. Med. 7 (2001), 393-395 and Anderson et al., 2001, Gage, F. H., 200 and Prockop, Science 276 (1997), 71-74, wherein the extraction and culture of those cells is described.

Media for isolating and propagating stem cells can have any of several different formulas, as long as the cells obtained have the desired characteristics, and can be propagated further. Suitable sources include Iscove's modified Dulbecco's medium (IMDM), Gibco, #12440-053; Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; [beta]-mercaptoethanol, Sigma #M7522; human recombinant basic fibroblast growth factor (bFGF), Gibco #13256-029. Exemplary serum-containing ES medium and conditions for culturing stem cells are known, and can be optimized appropriately according to the cell type. Media and culture techniques for particular cell types referred to in the previous section are provided in the references cited herein.

As mentioned before, several sources for ES cells are at the disposal of the skilled person of which human stem cells are preferred for most of the embodiments of the present invention, in particular for therapeutic purposes such as transplantation. Human embryonic stem cells and their use for preparing different cell and tissue types are also described in Reprod. Biomed. Online 4 (2002), 58-63. Embryonic stem cells can be isolated from blastocysts of members of the primate species (Thomson et al., Proc. Natl. Acad. Sci. USA 92 (1995), 7844). Human embryonic germ (EG) cells can be prepared from primordial germ cells present in human fetal material taken about 8-11 weeks after the last menstrual period. Suitable preparation methods are described in Shamblott et al., Proc. Natl. Acad. Sci. USA 95 (1998), 13726. Methods for making cells that resemble embryonic stem cells or embryonic germ cells 30 in morphology and pluripotency derived from primordial germ cells isolated from human embryonic tissue, such as from the gonadal ridges of human embryo, are described in U.S. Pat. No. 6,245,566.

Recently, is has been reported that exfoliated human deciduous tooth, a comparable very accessible tissue, contains multipotent stem cells that were identified to be a population of highly proliferative, clonogenic cells capable of differentiating into a variety of cell types including neural cells, adipocytes, and odontoblasts; see Miura et al., Proc. Natl. Acad. Sci. USA 100 (2003), 5807-5812. After in vivo transplantation, those cells were found to be able to induce bone formation, generate dentin, and survive in mouse brain along with expression of neural markers. Furthermore, multilineage potential of homozygous stem cells derived from metaphase II oocytes has been described by Lin et al. in Stem Cells 21 (2003), 152-161. Various sources of precursor cells in postnatal muscles and the factors that may enhance stem cell participation in the formation of new skeletal and cardiac muscle in vivo are reviewed in Grounds et al., J. Histochem. Cytochem. 50 (2002), 589-610. Purification of rare hematopoietic stem cell(s) (HSC) to homogeneity that home to bone marrow is described in U.S. application US2003/0032185. These adult bone marrow cells are described to have tremendous differentiative capacity as they can also differentiate into epithelial cells of the liver, lung, GI tract, and sldn. This finding may contribute to clinical treatment of genetic disease or tissue repair. Furthermore, techniques such as nuclear transfer for embryo reconstruction may be employed wherein diploid donor nuclei are transplanted into enucleated MII oocytes. This technology along with other procedures that aid in the establishment of customized embryonic stem (ES) cell lines that are genetically identical to those of the recipient have been reviewed by Colman and Kind, Trends Biotechnol. 18 (2000), 192-196. In order to avoid graft rejection associated with allogenic or xenogenic cells in transplantation syngenic or autologous cells and recipients are preferably used in the corresponding embodiments of the invention. In view of the recently discovered sources of stem cells such as from the bone marrow and tooth it should be possible to accomplish this demand without the need to resort to embryonic cells and tissue. Alternatively, cells may be genetically manipulated to suppress relevant transplantation antigens, see also infra, immunosuppressive agents may be used.

The field of stem cell technology is being reviewed by Kiessling and Anderson, Harvard Medical School, in Human Embryonic Stem Cells: An Introduction to the Science and Therapeutic Potential; (2003) Jones and Bartlett Publishers; ISBN: 076372341X.

In order to avoid the use of for example human embryos as the donor for stem cells, which however seems to be justifiable at least under certain circumstances, it may even be possible to employ transgenic non-human animals, in particular mammals, as source for embryonic stem cells. For example, compositions and methods for making transgenic swines to be used as xenograft donors are described in U.S. Pat. No. 5,523,226. Likewise, international application WO97/12035 describes methods of producing transgenic animals for xenotransplantation. Furthermore, immunologically compatible animal tissue, suitable for xenotransplantation into human patients, is described in international application WO01/88096. Methods for making embryonic germ cells from porcine are described for example in U.S. Pat. No. 6,545,199.

Stem cells can be propagated continuously in culture, using a combination of culture conditions that promote proliferation without promoting differentiation. Traditionally, stem cells are cultured on a layer of feeder cells, typically fibroblast type cells, often derived from embryonic or fetal tissue. The cell lines are plated to near confluence, usually irradiated to prevent proliferation, and then used to support when cultured in medium conditioned by certain cells (e.g. Koopman and Cotton, Exp. Cell 154 (1984), 233-242; Smith and Hooper, Devel. Biol. 121 (1987), 1-91), or by the exogenous addition of leukemia inhibitory factor (LIF). Such cells can be grown relatively indefinitely using the appropriate culture conditions.

International application WO03/010303 and Mummery et al., Circulation 107 (2003), 2733-2740, disclose experiments with human embryonic stem (hES) cells differentiating to cardiomyocytes, wherein said hES cells were co-cultured with visceral-endoderm (VE)-like cells from the mouse. In those experiments the mouse endoderm cells replace the commonly used mouse fibroblast feeder cells and are used for the induction of cardiomyocyte differentiation in hES cells that do not undergo spontaneous cardiogenesis.

Accordingly, Mummery et al. do not teach a method of providing tissue or tissue-like structures allowing integration and alignment of said endoderm cells with the hES cells. To the contrary, the use of mouse endoderm cells already indicates that those cells are removed when using the differentiated cardiomyocytes for further applications including transplantation. Also in contrast thereto, the methods of the present invention typically employ stem cells and embryonic cells originating from the same species, most preferably from human.

In the absence of feeder cells, exogenous leukemia inhibitory factor (LIF), or conditioned medium, ES or EG cells spontaneously differentiate into a wide variety of cell types, including cells found in each of the endoderm, mesoderm, and ectoderm germ layers. With the appropriate combinations of growth and differentiation factors, however, cell differentiation can be controlled. For example, mouse ES and EG cells can generate cells of the hematopoietic lineage in vitro (Keller et al., Mol. Cell Biol. 13 (1993), 473-486; Palacios et al., Proc. Natl. Acad. Sci. USA 92 (1995), 7530-7534; Rich, Blood 86 (1995), 463-472). Additionally, mouse ES cells have been used to generate in vitro cultures of neurons (Bain et al., Developmental Biology 168 (1995), 342-357; Fraichard et al., J. Cell Science 108 (1995), 3161-3188), cardiomyocytes (heart muscle cells) (Klug et al., Am. J. Physiol. 269 (1995), H1913-H1921), skeletal muscle cells (Rohwedel et al., Dev. Biol. 164 (1994), 87-101), vascular cells (Wang et al., Development 114 (1992), 303-316). U.S. Pat. No. 5,773, 255 relates to glucose-responsive insulin secreting pancreatic beta cell lines, U.S. Pat. No. 5,789,246 relates to hepatocyte precursor cells. Hepatic differentiation of murine embryonic stem cells is also described in Jones et al., Exp. Cell Res. 272 (2002), 15-22.

Other progenitors of interest include but are not limited to chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells. Embryonic stem cell differentiation models for cardiogenesis, myogenesis, neurogenesis, epithelial and vascular smooth muscle cell differentiation in vitro have been generally described in Guan et al., Cytotechnology 30 (1999), 211-226.

In certain embodiments of the invention, differentiation is promoted by withdrawing one or more medium component(s) that promote(s) growth of undifferentiated cells, or act(s) as an inhibitor of differentiation. Examples of such components include certain growth factors, mitogens, leukocyte inhibitory factor (LIF), and basic fibroblast growth factor (bFGF). Differentiation may also be promoted by adding a medium component that promotes differentiation towards the desired cell lineage, or inhibits the growth of cells with undesired characteristics.

In accordance with this invention, populations of differentiated cells are depleted of relatively undifferentiated cells and/or of cells of undesired cell types by using a selection system that is 30 lethal to the undesired cells and cell types, i.e. by expressing a selectable marker gene that renders cells of a specific cell type resistant to a lethal effect of an external agent, under control of a regulatory sequence that causes the gene to be preferentially expressed in the desired cell type and/or at a certain stage of development. To accomplish this, the cells are genetically altered before the process used to differentiate the cells into the desired lineage for therapy, in a way that the cells comprise a selectable marker operably linked to a first cell type-specific regulatory sequence specific for the desired first cell type. An exemplary construct is given in FIG. 1.

Any suitable expression vector for this purpose can be used. Suitable viral vector systems for producing stem cells altered according to this invention can be prepared using commercially available virus components. The introduction of the vector construct or constructs into the embryonic stem cells occurs in a known manner, e.g. by transfection, electroporation, lipofection or with the help of viral vectors. Viral vectors comprising effector genes are generally described in the publications referenced to in the last section. Alternatively, vector plasmids can be introduced into cells by electroporation, or using lipid/DNA complexes. Exemplary is the formulation Lipofectamine 2000™, available from Gibco/Life Technologies. Another exemplary reagent is FuGENE™ 6 Transfection Reagent, a blend of lipids in non-liposomal form and other compounds in 80% ethanol, obtainable from Roche Diagnostics Corporation. Preferably, the vector constructs and transfection methods described in international application WO02/051987 are used, the disclosure content of which is incorporated herein by reference.

Resistance genes per se are known. Examples for these are nucleoside and aminoglycoside-antibiotic-resistance genes for, e.g. puromycin (puromycin-N-acetyltransferase), streptomycin, neomycin, gentamycin or hygromycin. Further examples for resistance genes are dehydrofolate-reductase, which confers a resistance against aminopterine and methotrexate, as well as multi drug resistance genes, which confer a resistance against a number of antibiotics, e.g. against vinblastin, doxorubicin and actinomycin D. In a particularly preferred embodiment of the present invention, said selectable marker confers resistance to puromycin. Puromycin is particularly suited for the fast elimination of non-cardiac cells in adherent culture of transgenic EBs. Furthermore, drug selection of cardiac cells can be implemented entirely in the suspension culture of transgenic EBs. Hence, it could also be shown that purified ES cell-derived cardiomyocytes survive much longer in culture than untreated counterparts. Moreover, the elimination of undifferentiated ES cells during drug selection process has itself been shown to have a clear positive effect on viability and longevity of such differentiated ES cell-derived cells as cardiomyocytes. In addition, it could be surprisingly shown that the release from surrounding non-differentiated cells induces proliferation of cardiomyocytes. Thus, the drug selection possesses both a purifying and multiplying effect.

In a preferred embodiment of the invention, said ES cell of said ES cell-derived first cell type 5 comprises a reporter gene, wherein said reporter is operably linked to a cell type-specific regulatory sequence specific for said first cell type. This type of vector has the advantages of providing visualization of differentiation, definition of the time point for beginning of drug selection, visualization of drug selection and tracing of the fate of purified cells grafted in recipient tissue. Such vectors, which are preferably employed in accordance with the methods of the present invention, are described in international application WO02/051987. Usually, said cell type-specific regulatory sequence of the reporter gene is substantially the same as said first cell type-specific regulatory sequence of the marker gene. This can advantageously be achieved by putting said marker gene and said reporter gene into the same recombinant nucleic acid molecule, i.e. vector used for stem cell transfection, preferably such that said marker gene and said reporter gene are contained on the same cistron. An example for a dicistronic cardiac specific drug resistance cassette—reporter vector is shown in FIG. 1. The reporter can be of any kind as long as it is non-damaging for the cell and confers an observable or measurable phenotype. According to the present invention, the green fluorescent protein (GFP) from the jellyfish Aequorea victoria (described in international applications WO95/07463, WO96/27675 and WO95/121191) and its derivates "Blue GFP" (Heim et al., Curr. Biol. 6 (1996), 178-182 and Redshift GFP" (Muldoon et al., Biotechniques 22 (1997), 162-167) can be used. Particularly preferred is the enhanced green fluorescent protein (EGFP). Further embodiments are the enhanced yellow and cyan fluorescent proteins (EYFP and ECFP, respectively) and red fluorescent proteins (DsRed, HcRed). Further fluorescent proteins are known to the person skilled in the art and can be used according to the invention as long as they do not damage the cells. The detection of fluorescent proteins takes place through per se known fluorescence detection methods; see, e.g., Kolossov et al., J. Cell Biol. 143 (1998), 2045-2056. Alternatively to the fluorescent proteins, particularly in in vivo applications, other detectable proteins, particularly epitopes of those proteins, can also be used. Also the epitope of proteins, though able to damage the cell per se, but whose epitopes do not damage the cells, can be used; see also international application WO02/051987.

For the selection of stably transfected ES cells vector constructs contain a further selectable marker gene, which confers e.g. a resistance against an antibiotic, e.g. neomycin. Of course, other known resistance genes can be used as well, e.g. the resistance genes described above in association with the fluorescent protein encoding genes. The selection gene for the selection for stably transfected ES cells is under the control of a different promoter than that which regulates the control of the expression of the detectable protein. Often constitutively active promoters are used, e.g. the PGK-promoter.

The use of a second selection gene is advantageous for the ability to identify the successfully transfected clones (efficiency is relatively low) at all. Otherwise a smothering majority of non-transfected ES cells may exist and during differentiation e.g. no EGFP-positive cells might be detected.

In a further embodiment of the invention the cells can be manipulated additionally, so that specific tissues are not formed. This can occur for instance by inserting repressor elements, e.g. a doxicyclin inducible repressor element. Thereby, a possible contamination of the desired differentiated cells with pluripotent, potentially tumorigenic cells can be excluded. The desired first cell type intended for the stem cell to differentiate to may be of any kind and includes but is not limited to neuronal cells, glial cells, cardiomyocytes, glucose-responsive insulin-secreting pancreatic beta cells, hepatocytes, astrocytes, oligodendrocytes, chondrocytes, osteoblasts, retinal pigment epithelial cells, fibroblasts, keratinocytes, dendritic cells, hair follicle cells, renal duct epithelial cells, vascular endothelial cells, testicular progenitors, smooth and skeletal muscle cells; see also supra.

In a particular preferred embodiment of the invention, said first cell type are cardiomyocytes. For this embodiment, said first cell type-specific regulatory sequence is preferably atrial- and/or ventricular-specific. Corresponding regulatory sequences, i.e. cardiac-specific promoters are described for Nkx-2.5 specific for very early cardiomyocytes and mesodermal precursor cells, respectively (Lints et al., Development 119 (1993), 419-431); human-cardiac-α-actin specific for heart tissue, (Sartorelli et al., Genes Dev. 4 (1990), 1811-1822), and MLC-2V specific for ventricular heart muscle cells (O'Brien et al., Proc. Natl. Acad. Sci. U.S.A. 90 (1993), 5157-5161 and international application WO96/16163). A cardiac-specific alpha-myosin heavy chain promoter is described in Palermo et al., Cell Mol. Biol. Res. 41 (1995), 501-519; Gulick et al., J. Biol. Chem. 266 (1991), 9180-91855; the myosin light chain-2v (MLC2v) promoter also by Lee et al., Mol. Cell Biol. 14 (1994), 1220-1229; Franz et al., Circ. Res. 73 (1993), 629-638; see also expression of the atrial-specific myosin heavy chain AMHC 1 and the establishment of anteroposterior polarity in the developing chicken heart described in Yutzey et al., Development 120 (1994), 871-883.

Muller et al. describe the selection of ventricular-like cardiomyocytes from ES cells in vitro by use of enhanced green fluorescent protein (EGFP) under transcriptional control of the ventricular-specific 2.1 kb myosin light chain-2v (MLC-2v) promoter and the 0.5 kb enhancer element of the cytomegalovirus (CMV(enh)); see Muller et al., FASEB J. 14 (2000), 2540-2548. This publication also describes electrophysiological studies which may be similarly performed with the in vitro-generated tissue and tissue-like structures of the present invention. Particularly in accordance with embodiments relating to in vitro differentiated cardiomyocytes, it is preferred to use fibroblasts as said at least one embryonic second cell type. As shown in the examples, the co-culture and co-transplantation, respectively, of ES cell-derived cardiomyocytes and embryonic fibroblasts resulted in cardiac tissue formation and successful replacement therapy. Those fibroblasts may not necessarily be derived from embryos but can also be generated de novo from ES cells in accordance with the method of the present invention. Thus, ES cells are transfected with a recombinant nucleic acid molecule comprising a marker and optionally reporter gene operatively linked to a cell type-specific regulatory sequence, i.e. fibroblast-specific promoter such as the a2 (I) collagen promoter though also active in bone cells (Lindahl et al., J. Biol. Chem. 277 (2002), 6153-6161; Zheng et al., Am. J. Pathol. 160 (2002), 1609-1617; Antoniv et al., J. Biol. Chem. 276 (2001), 21754-21764; see also Finer et al., J. Biol. Chem. 262 (1987), 13323-13333; Bou-Gharios et al., J. Cell Biol. 134 (1996), 1333-1344; Zheng et al., Am. J. Pathol. 160 (2002), 1609-1617; Metsaranta et al., J. Biol. Chem. 266 (1991) 16862-16869).

However, for other embodiments fibroblasts may be used as well and/or alternatively other supporting cells such as endothelial cells, etc. and derivatives thereof.

In a further preferred embodiment, the method of the present invention further comprises culturing said at least two cell types in the presence of an embryonic or embryonic stem (ES) cell-derived third cell type. Said third cell type may be any cell type mentioned above.

Preferably, said third cell type are endothelial cells. Hence, either embryonic endothelial cells or ES cell-derived endothelial cells may be used. In the latter embodiment, said endothelial cells are derived from ES cells transfected with a vector construct as generally described before, wherein said cell type-specific regulatory sequence is an endothelial-specific promoter; see, e.g., vascular endothelial-cadherin promoter described by Gory et al., Blood 93 (1999), 184-192; the Tie-2 promoter/enhancer by Schlaeger et al., Proc. Natl. Acad. Sci. USA 94 (1997), 3058-3063; and the Flk-1 promoter/enhancer by Kappel et al., Biochem. Biophys. Res. Commun. 276 (2000), 1089-1099.

Further cell and tissue type-specific promoters are known; see, e.g., chondrocyte-specific pro-alphaI (II) collagen chain (collagen 2) promoter fragment described by Zhou et al., J. Cell Sci. 108 (1995), 3677-3684; neural alpha-1-tubulin-specific promoter described in Gloster et al., J. Neurosci. 14 (1994); 7319-7330; and glial fibrillary acidic protein (GFAP) promoter in Besnard et al., J. Biol. Chem. 266 (1991), 18877-18883. Further examples for tissue-specific promoters are those which are active in glia cells, hematopoietic cells, neuronal cells, preferably embryonal neuronal cells, endothelial cells, cartilage cells or epidermal cells as well as insulin-secreting β cells. "Tissue-specific" is to be subsumed under the term "cell-specific".

Further examples for non-heart-specific promoters are: PECAM1, FLK-1 (endothelium), nestine (neuronal precursor cells), tyrosin-hydroxylase-1-promoter (dopaminergic neurons), smooth muscle α-actin, smooth muscle myosin (smooth muscles), α1-fetoprotein (endoderm), smooth muscle heavy chain (SMHC minimal promoter (specific for smooth muscles, Kallmeier et al., J. Biol. Chem. 270 (1995), 30949-30957).

The term development-specific promoter refers to promoters that are active during certain points of time during development. Examples for such promoters are the β-MHC promoter that is expressed during embryonal development in the ventriculum of the mouse and is superseded by the α-MHC promoter in the prenatal phase. NKx2.5, a promoter during the early mesoderm/heart development, atrial-natriuretic factor, a marker of the early embryonal heart with exception of the pacemaker that is down-regulated also in later developmental stages, Flk-1, an endothelium-specific promoter that is active during the early vasculogenesis, intron 2-segment of the nestine gene that is expressed in neuronal precursor cells (embryonal neurons and glia cells) and adult glia cells (partially still able to divide) (Lothian and Lendahl, Fur. J. Neurosci. 9 (1997), 452-462U).

Figure 2A:
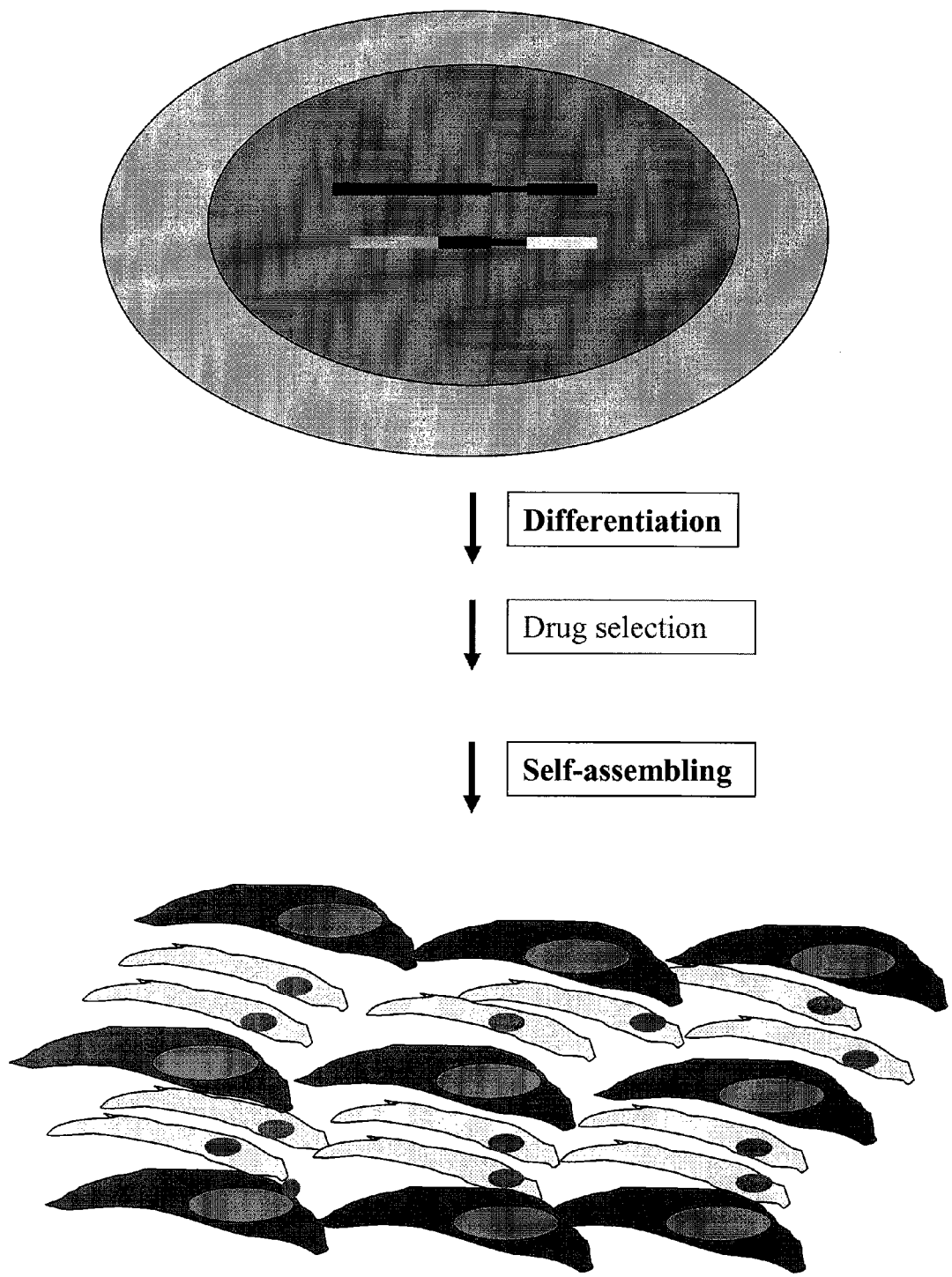
FIG. 2: Two vectors—(A) One transgenic ES cell clone; (B) Two transgenic ES cell clones.
Figure 2B:
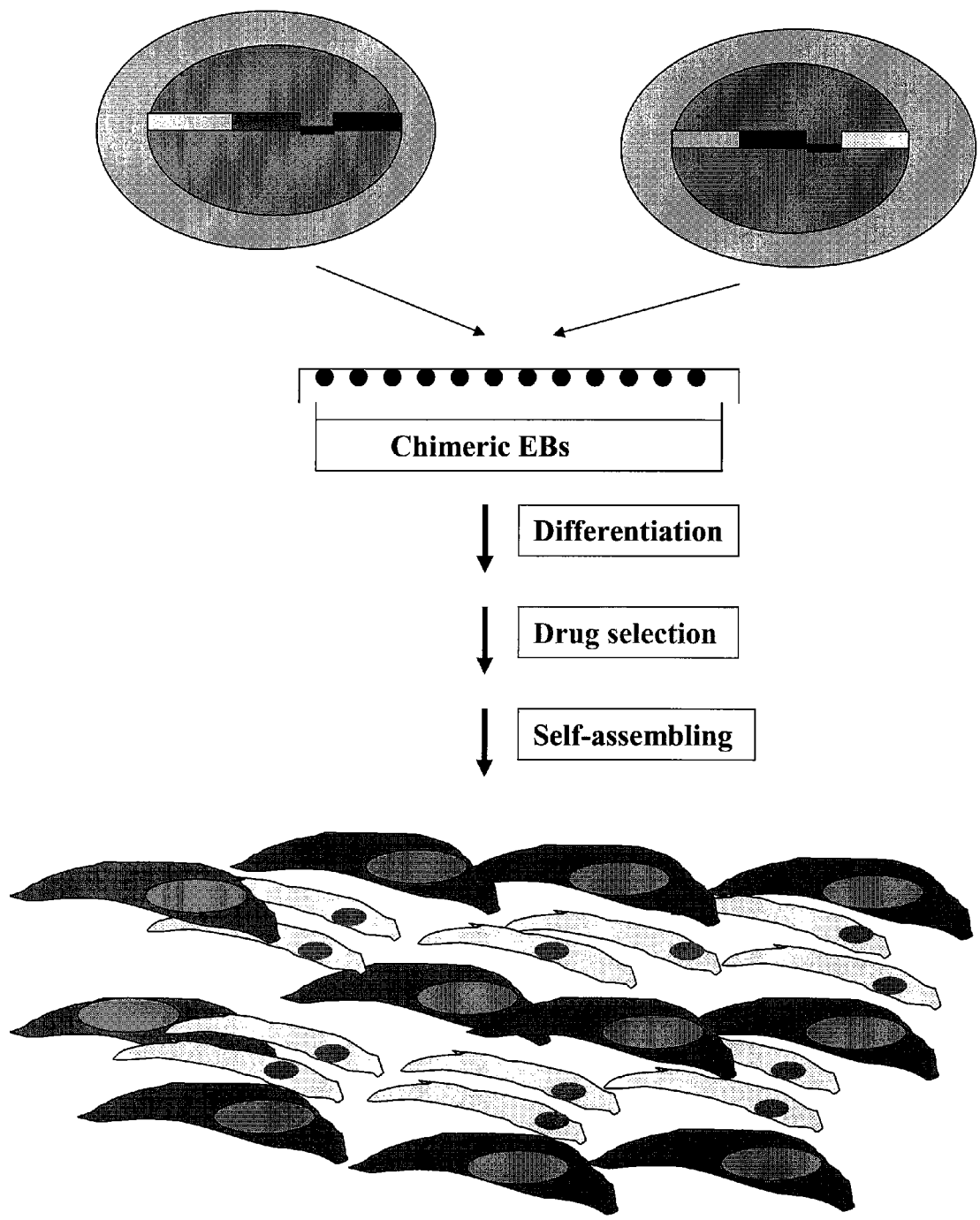
Figure 3:
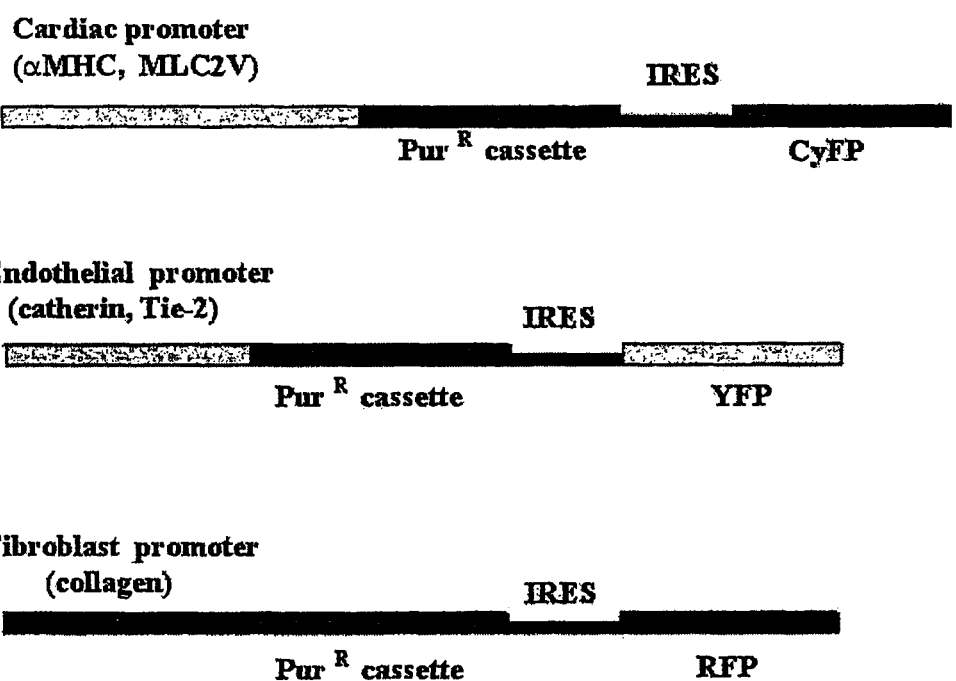
FIG. 3: Three vectors—(A) Vector constructs; (B) One transgenic ES cell clone; (C) Three transgenic ES cell clones.
Figure 3:
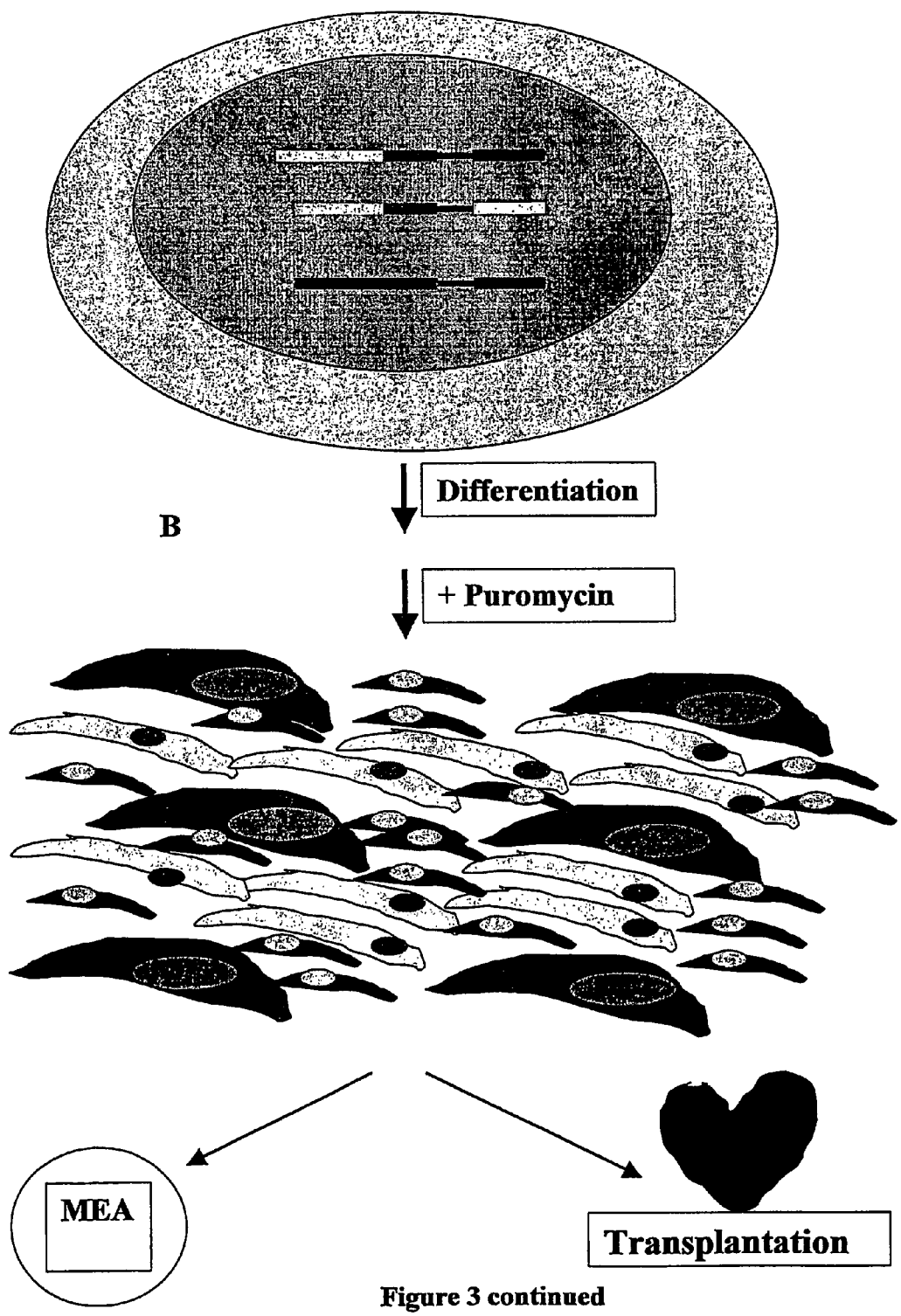
Figure 3:
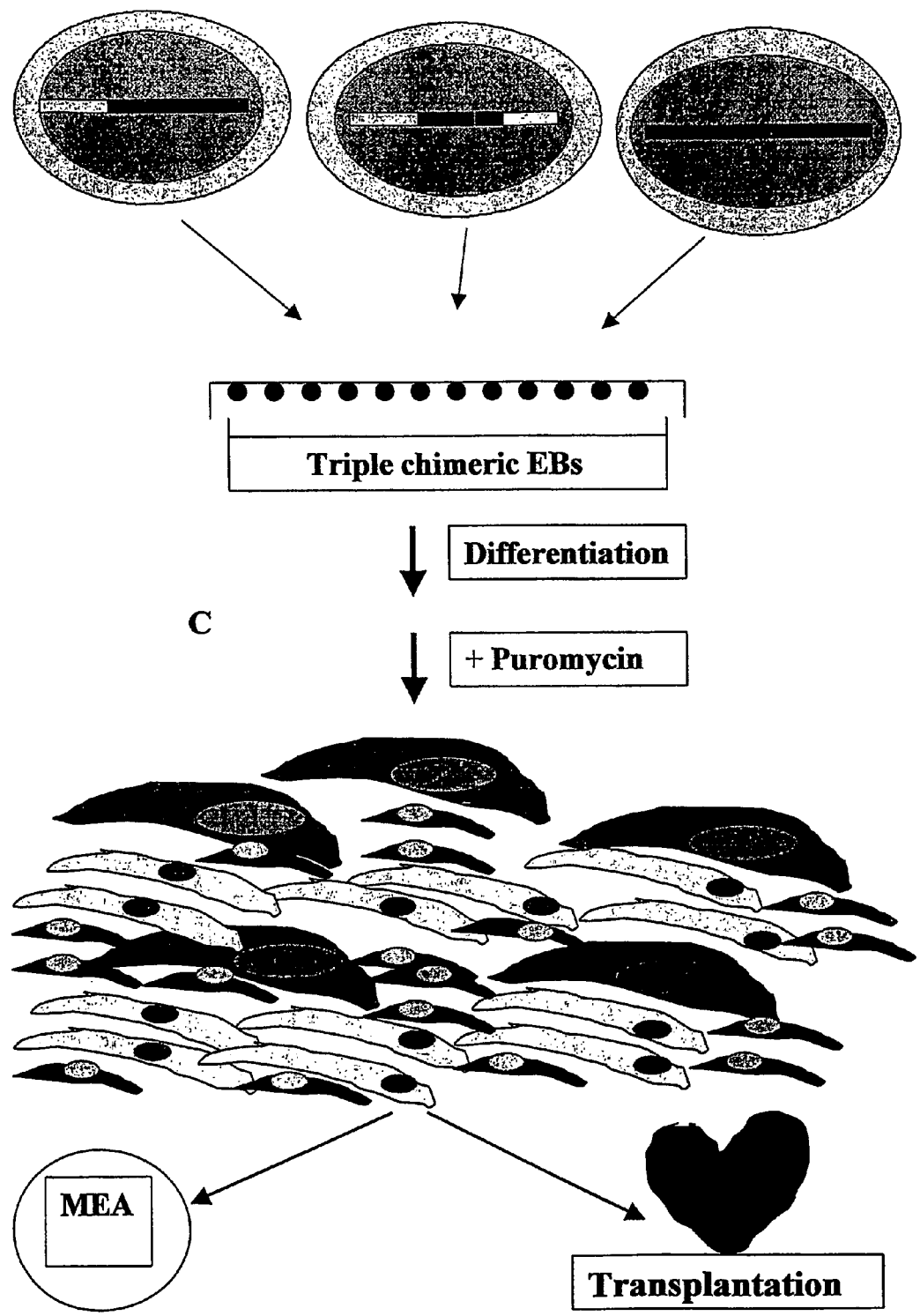

In the mentioned embodiments those vectors shown in FIGS. 1 to 3 are preferably used. The present invention also relates to co-cultures of cells as defined in the methods hereinbefore as well as to tissue obtainable by the method of the invention. Cells and tissue prepared according to this invention can be used for a variety of commercially important research, diagnostic, and therapeutic purposes. Because the cell populations of this invention are depleted of undifferentiated cells, they can be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000).

One main object of the present invention is however the provision of cells and tissue for use in transplantation For example, differentiated cells of this invention can also be used for tissue reconstitution or regeneration in a human patient in need thereof. The cells are administered in a manner that permits them to graft to the intended tissue site and reconstitute or regenerate the functionally deficient area. Thus, the present invention particularly concerns a method of improving tissue repair and/or organ function in a mammal comprising the steps of:

(a) introducing a cellular inoculum comprising a co-culture of preferably transgenic stem cells in which differentiation has been initiated or corresponding tissue to at least a portion of the previously damaged area of the tissue; and (b) allowing said introduced cellular inoculum to engraft in situ as viable cells or tissue situated within the previously damaged area of the tissue, wherein the engraftment results in improved tissue and/or organ function in said mammal.

Select examples are used to illustrate the potential of stem cells, both in the sense of their ability to differentiate into specific cell types and in the sense of their power to treat various diseases and conditions such as Parkinson disease, spinal cord injuries, diabetes, and cardiac disease have been reviewed in Pfendler and Kawase in Obstet. Gynecol. Surv. 58 (2003), 197-208. All those conditions can be treated by use of the of the above-described cells and tissue.

Figure 6:
FIG. 6: Puromycin-selected ES cell-derived cardiomyocytes successfully engrafted in the cryo-infarcted areas when co-transplanted with syngenic fibroblasts. A, a heart 40 days after transplantation under combined transmission-fluorescent light; B, C, engrafted EGFP-positive (C) ES cell-derived cardiomyocytes show cross striation after α-actinin immunostaining (B).
Figure 6:
Figure 6:

In a particular aspect, the present invention relates to a method for markedly improving cardiac function and repairing heart tissue in a living mammalian subject after the occurrence of a myocardial infarction or tissue damage. The method is a surgical technique which introduces and implants embryonic stem cells, i.e. mammalian embryonic stem cell-derived cardiomyocytes along with supporting embryonic cells such embryonic fibroblasts into the infarcted or damaged area of the myocardium. After implantation, the cells form stable grafts and survive indefinitely within the infarcted or damaged area of the heart in the living host. The demonstrated beneficial effects of the method include a decreased infarcted area and improved cardiac function; see FIG. 6.

Hence, the instant invention also concerns a method for improving the cardiac function in a mammal after a myocardial infarct, said method comprising the steps of:
(a) culturing undifferentiated mammalian embryonic stem (ES) cells comprising a resistance gene and a reporter gene under the control of the same cardiac-specific promoter in vitro in a culture medium containing the selective agent for the resistance gene under conditions allowing differentiation of said ES cells into cardiomyocytes;
(b) isolating said differentiated cardiomyocytes and/or eliminating non-differentiated cells, optionally along with cells differentiating towards irrelevant cell types from said cardiomyocytes in the course of differentiation;
(c) subsequently co-transplanting said cardiomyocytes with embryonic or ES cell-derived fibroblasts and/or endothelial cells to at least a portion of the previously infarcted area of the heart tissue; and
(d) allowing said introduced cellular inoculum to engraft in situ as viable cells situated within the previously infarcted area of the heart tissue, wherein the engraftment results in improved cardiac function in said mammal.

Similarly as for the embodiments described hereinbefore, said resistance gene and said reporter gene are contained in a bicistronic vector and are preferably separated by an IRES. Particularly preferred is the use of a construct, wherein said resistance gene confers resistance to puromycin, said marker is EGFP and said promoter is the cardiac αMHC promoter; see FIG. 3. Implantation of embryonic stem cells in which differentiation has been initiated and determining cardiac function can be done as described in the examples and cited references, or, e.g., as described in U.S. Pat. No. 6,534,052.

U.S. Pat. No. 5,733,727 describes myocardial grafts of skeletal myoblasts or cardiomyocytes, and cellular compositions and methods useful in obtaining the grafts. Those myocardial grafts are described to be stable and for use in, for example, delivery of recombinant proteins directly to the heart. While this US patent only describes the common approach of generating cardiomyocytes from ES cells and their use in transplantation and as a vehicle for delivering recombinant proteins to the heart, its teaching may be applied to the tissue and tissue-like structures obtained in accordance with the present invention. Thus, in particular the in vitro generated cardio-tissue like structure of the present invention can be used for the delivery of therapeutic proteins such as angiogenic factors (as exemplified by basic and acidic Fibroblast Growth Factor; Transforming Growth Factor-β, Vascular Endothelial Growth Factor and Hepatocyte Growth Factor) to induce neovascularization. Similarly, grafts expressing neurotrophic agents near an infarcted region may be used to ameliorate the arrhythmogenesis associated with the border zone. These and many other candidate substances for targeted delivery to the heart will be apparent to those skilled in the art.

As mentioned before, in accordance with the present invention any of said at least two cell types such as a main cell type and corresponding supporting cells may be derived from ES cells. Hence, in a further aspect the present invention relates to a method of modeling and/or obtaining tissue or tissue-like structures comprising the following steps:
(a) transfecting one or more multi- or pluripotent cells with recombinant nucleic acid molecules comprising a first and a second cell type-specific regulatory sequence operably linked to at least one selectable marker, wherein said second cell type is different from said first cell type;
(b) culturing the cells under conditions allowing differentiation of the cells; and
(c) isolating cells of at least two differentiated cell types and/or eliminating non-differentiated cells, optionally along with cells differentiating towards irrelevant cell types from cell types of interest that activate the selectable marker in the course of differentiation.

Similarly as in the previous methods the generation of more than two cell types is desired. Therefore, the method preferably comprises transfecting said one or more cells with recombinant nucleic acid molecules comprising at least one further cell type-specific regulatory sequence operably linked to at least one selectable marker, wherein said at least one further cell type is different from said first and second cell type. For use in the method, said recombinant nucleic acid molecules are comprised in the same vector or different vectors. The principle behind those options is shown in FIGS. 2 and 3 and explained in the examples.

The cell type may be selected from the group consisting of neuronal cells, glial cells, cardiomyocytes, glucose-responsive insulin-secreting pancreatic beta cells, hepatocytes, astrocytes, oligodendrocytes, chondrocytes, osteoblasts, retinal pigment epithelial cells, fibroblasts, keratinocytes, dendritic cells, hair follicle cells, renal duct epithelial cells, vascular endothelial cells, testicular progenitors, smooth and skeletal muscle cells; see also supra.

Promoters that are preferably used if the preparation of cardiac tissue is desired by differentiating the transfected stem cell(s) into cardiomyocytes, fibroblasts and optionally endothelial cells comprise those described hereinbefore. Similarly, for producing neuronal tissue one or more stem cells, for example multipotent neural stem cells, can be used and genetically engineered in accordance with the present invention to differentiate into neurons, astrocytes, and oligodendrocytes. The same rationale applies for the generation of for example liver or pancreatic tissue. Regulatory sequences of corresponding cell type-specific promoters can be obtained from the literature; see, e.g., "medline" and NCBI.

It is to be understood that when performing the method of the invention, said one or more recombinant nucleic acid molecules can be transfected concomitantly or subsequently into said one or more cells.

As explained in the examples and shown in FIGS. 2 and 3, the method of the invention can be performed in different ways. First, as preferably described herein, a multiple transgenic ES cell clone is produced stably transfected with a certain number of vectors with a drug selection cassette driven by specific promoters according to the cell types constituting the desirable tissue type. Thus, at least one of said ES cells or cell clone thereof is transfected and selected, wherein said cell or cell clone contains recombinant nucleic acid molecules with at least two different cell type-specific regulatory sequences. In such a variant all emerging cell types have the origin from one common ES cell clone predecessor and the resulting ratio between different cell components depends on the relative differentiation rate of each of them. Alternatively, at least two different ES cells or clones thereof are transfected and selected, wherein said at least two different cells or cell clones contain recombinant nucleic acid molecules with different cell type-specific regulatory sequences. By this approach a number of transgenic ES cell clones is generated where each single clone possesses only one vector with a drug-resistant cassette driven by one of the cell type-specific promoters. For tissue modeling the relevant clones should be mixed in the initial phase of differentiation ("hanging drops" or "mass culture") in order to form ES cell aggregates (EBs) where, after drug selection, emerging cell types have origin from different corresponding ES cell clones and the final ratio of the cell components also depends on and can be controlled by the initial ratio between different ES cell lines. This method preferably results in cell aggregates that are chimeric embryoid bodies (EBs).

Irrespective of the particular embodiment of the method of the invention, it is preferred that at least two of said selectable markers are operably linked to said different cell type-specific regulatory sequences are identical. As mentioned before, those markers or marker genes are preferably selectable markers which confer resistance to a cell toxic agent, preferably puromycin, methothrexate, or neomycin.

As already described with respect to the method of the first aspect of the instant invention, said one or more of said recombinant nucleic acid molecules preferably further comprise a reporter operably linked to said cell type-specific sequence; see supra. Herein preferred as well are the different color versions of enhanced green fluorescent protein (EGFP), in particular EYFP (yellow), ECFP (blue) and/or hcRFP (red), operably linked to different cell type-specific sequences. Likewise preferred is that said selectable marker and said reporter are expressed from a bicistronic vector, preferably wherein said selectable marker and said reporter are separated by one or more internal ribosomal entry sites (IRES), which are operably linked to at least one of said genes.

As mentioned above, the method of the present invention is preferably performed such that it allows self-assembly of the different cell types, for example into the desired tissue or tissue-like structures. The stem cells are in a preferred embodiment of the invention available in form of aggregates that are known as embryoid bodies. International application WO02/051987 describes a protocol to obtain embryoid bodies. The manufacturing takes place preferably with the "hanging drop" method or by methylcellulose culture (Wobus et al., Differentiation 48 (1991), 172-182).

Alternatively to this, spinner flasks (stirring cultures) can be used as culture method. Therefore, the undifferentiated ES cells are introduced into stirring cultures and are mixed permanently according to an established procedure. For example, 10 million ES cells are introduced into 150 ml medium with 20% FCS and are stirred constantly with the rate of 20 rpm., wherein the direction of the stirring motion is changed regularly. 24 hours after introduction of the ES cells an extra 100 ml medium with serum is added and thereupon 100-150 ml of the medium is exchanged every day (Wartenberg et al., FASEB J. 15 (2001), 995-1005). Under these culture conditions large amounts of ES cell-derived cells, i.e. cardiomyocytes, endothelial cells, neurons etc., depending on the composition of the medium, can be obtained. The cells are selected by means of the resistance gene either still within the stirring culture or after plating, respectively.

Alternatively to this, the EBs differentiated in the hanging drop might be not plated, but kept simply in suspension. Even under these conditions a progression of a differentiation could be observed experimentally. The washing off of the non-desired cell types can be done with mechanical mixing alone and addition of low concentration of enzyme (e.g. collagenase, trypsin); a single cell suspension is achieved with easy washing off of the non-desired cell types.

In one embodiment, the fate of the cell types and formation of cell aggregates and tissue as well as the physiological and/or developmental status of the cells or cell aggregates are analyzed, for example by isometric tension measurements, echocardiography and the like. Preferably, the status of the cells or cell aggregates is analyzed by monitoring the differentiation of electrical activity of the cells on an array, for example by recording the extracellular field potentials with a microelectrode array (MEA). For example, electrophysiological properties during the ongoing differentiation process of embryonic stem cells differentiating into cardiac myocytes can be followed by recordings of extracellular field potentials with microelectrode arrays (MEA) consisting of, e.g., 60 substrate-integrated electrodes; see Banach et al. Am. J. Physiol. Heart Circ. Physiol. 284 (2003), H2114-H2123. Multiple arrays of tungsten microelectrodes were used to record the concurrent responses of brain stem neurons that contribute to respiratory motor pattern generation; see Morris et al., Respir. Physiol. 121 (2000), 119-133.

The present invention also relates to cells, cell aggregates and tissue obtainable by the above described methods, wherein said cells are capable of differentiating into at least two cell types. Hence, said cells are preferably embryonic cell type—and/tissue-specific cells, most preferably cardiac tissue. Likewise, organs constituted from those cells, cell aggregates and tissue are subject of the present invention as well as implants or transplants comprising such cells, cell aggregates, tissue or organs. All of those can be used in a method of treatment of damaged tissue or organs in a subject comprising implanting or transplanting to the subject in need thereof. Hence, compositions such as pharmaceutical compositions comprising any one of those recombinant nucleic acid molecules, cells, cell aggregates, or tissue of the present invention as described herein are encompassed in the scope of the present invention. As described before, those compositions and methods of the invention can be used for a variety of purposes, for example for analyzing early steps of tissue formation during embryonic development or the influence of factors and compounds on this process.

In a still further embodiment, the present invention relates to transgenic non-human animals which can be generated from the mentioned ES cells and ES cell-derived cell types and cell aggregates; see supra. The generation of transgenic animals from ES cells is known in the art; see, e.g., A. L. Joyner Ed., Gene Targeting, A Practical Approach (1993), Oxford University Press. A general method for making transgenic non-human animals is described in the art, see for example international application WO94/24274.

In a particularly preferred aspect, the present invention relates to a method for improving the cardiac function in a mammal after a myocardial infarct, said method comprising the steps of:
(a) transfecting mammalian embryonic stem (ES) cells with a recombinant nucleic acid molecule comprising a resistance gene under the control of cardiac, fibroblast and optionally endothelium-specific regulatory sequences, and optionally comprising one or more reporters under the same specific regulatory sequences;
(b) culturing said ES cells in vitro in a culture medium containing the selective agent for the resistance gene under conditions allowing differentiation of said ES cells into cardiomyocytes, fibroblasts and optionally endothelial cells;

(c) eliminating from said differentiated cardiomyocytes, fibroblasts and optionally endothelial cells non-differentiated cells, optionally along with cells differentiating towards irrelevant cell types; optionally (d) allowing integration and aligning of said differentiating cardiomyocytes, fibroblasts and optionally endothelial cells into cardiac-like tissue;

(e) subsequently co-transplanting said cardiomyocytes, fibroblasts and optionally endothelial cells or said tissue to at least a portion of the previously infarcted area of the heart tissue; and (f) allowing said introduced cells or tissue to engraft in situ as viable cells situated within the previously infarcted area of the heart tissue, wherein the engraftment results in improved cardiac function in said mammal. As mentioned before, said cardiomyocytes, fibroblasts and optionally endothelial cells are preferably derived from the same ES cell. However, cardiomyocytes, fibroblasts and optionally endothelial cells derived from different ES cells may be used as well. In those embodiments, said cardiac-specific regulatory sequence is preferably selected from promoters of αMHC, MLC2v, MLC1a, MLC2a and βMHC, said endothelium-specific regulatory sequence is preferably selected from promoters of Tie2, Tie1 and Catherin, and said fibroblast-specific regulatory sequence is preferably selected from promoters of collagen I; see supra. Similarly, said reporter for said cardiomyocytes, fibroblasts and optionally endothelial cells is independently preferably selected from the enhanced green fluorescent proteins ECFP (blue), EYFP (yellow) and hcRFP (red); see also FIG. 3 and the examples. Said resistance gene and said reporter are preferably separated by an internal ribosomal entry site (IRES).

In another example, neuroepithelial cells are generated and used to augment or replace cells damaged by illness, autoimmune disorders, accidental damage, or genetic disorder. Mouse ES cells can be induced to differentiate in vitro with retinoic acid to form neuronal and glial precursors, positive for astrocyte (GFAP) or oligodendrocyte (04) markers, then later into functional neurons (Fraichard et al., J. Cell Science 108 (1995), 3161-3188). Cells transplanted to adult brains were observed innervating the host striatum (Deacon et al., Exp. Neurology, 149 (1998), 28-41). Human and mouse EC cell lines can also differentiate into neurons. (Trojanowski et al., Exp. Neurology, 144 (1997), 92-97; Wojcik et al., Proc. Natl. Acad. Sci. USA, 90 (1993), 1305-1309). Transplantation of these neurons into rats subjected to cerebral ischemia promoted a degree of functional recovery (Borlongan et al., Exp. Neurology 149 (1998), 310-321). In accordance with the present invention, for this embodiment corresponding neuronal and glial specific promoters are used; see, e.g., Kawai et al., Biochim. Biophys. Acta 1625 (2003), 246-252, and Kugler et al., Gene Ther. 10 (2003), 337-347, for glial and neuronal specific promoters. Efficiency of embryoid body formation and hematopoietic development from embryonic stem cells in different culture systems is described for example in Dang et al., Biotechnol. Bioeng. 78 (2002), 442-453. In another use of the invention, ES cells or their differentiating or differentiated derivatives can be used for the generation of non cellular structures such as bone or cartilage replacements. In another use of the invention, ES cells or their differentiating or differentiated derivatives can be used for the generation of liver tissue. Regulatory sequences for cell type-specific expression can be obtained from the cited literature and common sources such as "medline" and NCBI. If desired, such cells may be genetically modified for purposes of gene therapy.

In a further aspect, the present invention relates to a vector or a composition of vectors comprising the recombinant nucleic acid molecules as defined in context with the methods of the present invention hereinbefore. In particular, the present invention relates to vectors and compositions of vectors comprising in sum at least two units of a resistance gene under the control of a cardiac, fibroblast and optionally endothelium-specific regulatory sequence, and optionally comprising one or more reporters under the same specific regulatory sequences as described before; see also FIG. 3A. Those vectors or vector compositions may be substantially isolated or may be present in a sample or, e.g., in one or more host cells useful for, e.g., propagation of the vectors.

In a particularly preferred embodiment, the present invention relates to arrays comprising a solid support and attached thereto or suspended thereon cells, cell aggregates or tissue obtained by the method of the present invention or being in the differentiation process. The use of planar microelectrode arrays for cultured cells and cell aggregates as biosensors is of particular interest. Such arrays generally consist of a substrate of glass, plastic or silicon over which a conductor, e.g. gold, platinum, indium-tin oxide, iridium, etc., is deposited and patterned. An insulating layer, e.g. photoresist, polyimide, silicon dioxide, silicon nitride, etc., is deposited over the conducting electrodes and interconnects and then removed in regions over the electrodes to define the recording sites. Cells are cultured directly on this surface and contact the exposed conductor at the deinsulated recording sites Depending on the size of the electrodes and the cells, recordings of electrical activity can be from a single cell or populations of cells including cell aggregates. Each electrode site is generally connected to the input of a high input impedance, low noise amplifier, with or without AC coupling capacitors, to allow amplification of the relatively small extracellular signals. Examples of such biosensors are described by Novak et al., IEEE Transactions on Biomedical Engineering BME-33 (2) (1986), 196-202; Drodge et al., J. Neuroscience Methods 6 (1986), 1583-1592; Eggers et al., Vac. Sci. Technol. B8 (6) (1990), 1392-1398; Martinoia et al., J. Neuroscience Methods 48 (1993), 115-121; Maeda et al., J. Neuroscience 15 (1995), 6834-6845; and Mohr et al., Sensors and Actuators B-Chemical 34 (1996), 265-269. An apparatus prepared and adapted for analyzing the above described arrays is also subject of the present invention.

The cells, cell aggregates, tissue, organ and methods of the present invention are particularly suited for use in drug screening and therapeutic applications. For example, differentiated stem cells of this invention can be used to screen for factors (such as solvents, small molecules, drugs, peptides, polynucleotides, and the like) or environmental conditions (such as culture conditions or manipulation) that affect the characteristics of differentiated cells. Particular screening applications of this invention relate to the testing of pharmaceutical compounds in drug research. It is referred generally to the standard textbook "In vitro Methods in Pharmaceutical Research", Academic Press, 1997, and U.S. Pat. No. 5,030, 015). Assessment of the activity of candidate pharmaceutical compounds generally involves combining the differentiated cells of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially) to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. It is referred to A. Vickers (pp 375-410 in "In vitro Methods in Pharmaceutical Research," Academic Press, 1997) for further elaboration.

Thus, in a further embodiment the present invention relates to methods for obtaining and/or profiling a test substance capable of influencing cell development and/or tissue structure formation comprising the steps of:

(a) contacting a test sample comprising a cell, a cell aggregate, a tissue or an organ prepared or differentiating according to a method of the present invention, with a test substance; and b) determining a phenotypic response in said test sample compared to a control sample, wherein a change in the phenotypic response in said test sample compared to the control sample is an indication that said test substance has an effect on cell development and/or tissue structure formation.

These methods can replace various animal models, and form novel human-based tests and extreme environment biosensors. In particular, the methods of the invention can be used for toxicological, mutagenic, and/or teratogenic in vitro tests. Since the cells and tissue obtained in accordance with the present invention more closely resemble the in vivo situation, the results obtained by the toxicological assays of the present invention are expected to correlate to in vivo teratogenicity of the tested compounds as well.

For example, compounds, in particular cardiac-active compounds can be tested in accordance with methods described in DE 195 25 285 A1; Seiler et al., ALTEX 19 Suppl. 1 (2002), 55-63; Takahashi et al., Circulation 107 (2003), 1912-1916, and Schmidt et al., Int. J. Dev. Biol. 45 (2001), 421-429; the latter describing an ES cell test (EST) used in a European Union validation study for the screening of embryotoxic agents by determining concentration-dependently the differentiation of ES cells into cardiac and myogenic cells.

Cells and tissue of the central nervous system (CNS) generated by the methods of the present invention or during differentiation in said methods can be tested, for example, in cell culture such as described in U.S. Pat. No. 6,498,018. Similarly, cells and tissue related to the liver can be tested; see, e.g., US application US2003/0003573. A further in vitro test procedure for the detection of chemically induced effects on embryonic development and for differentiation for the purpose of embryotoxicity/teratogenicity screening based on differentiated pluripotent embryonic stem (ES) cells from mice and rats using embryonic germ (EG) cells obtained from primoridial germ cells is described in international application WO97/01644 and can be adapted in accordance with teachings of the present invention.

Preferred compound formulations for testing do not include additional components such as preservatives, that have a significant effect on the overall formulation. Thus preferred formulations consist essentially of a biologically active compound and a physiologically acceptable carrier, e.g. water, ethanol, DMSO, etc. However, if a compound is liquid without an excipient the formulation may consist essentially of the compound itself. Furthermore, a plurality of assays may be run in parallel with different compound concentrations to obtain a differential response to the various concentrations. As known in the art, determining the effective concentration of a compound typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection.

Compounds of interest encompass numerous chemical classes, though typically they are organic molecules. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, nucleic acids, saccharides, fatty acids, steroids, purines, pyrimidines, derivatives, structural analogs or combinations thereof.

Compounds and candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. For example, inhibition of tumor-induced angiogenesis and matrix-metalloproteinase expression in confrontation cultures of embryoid bodies and tumor spheroids by plant ingredients used in traditional chinese medicine has been described by Wartenberg et al., Lab. Invest. 83 (2003), 87-98.

Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The compounds may also be included in a sample including fluids to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of the sample used is sufficient to allow for measurable detection, usually from about 0.1 µl to 1 ml of a biological sample is sufficient.

Test compounds include all of the classes of molecules described above, and may further comprise samples of unknown content. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like.

Samples of interest compounds are being assessed for potential therapeutic value, i.e. drug candidates.

The test compound may optionally be a combinatorial library for screening a plurality of compounds. Such a collection of test substances can have a diversity of about $10^3$ to about $10^5$, is usually successively reduced in running the method, optionally combined with others twice or more. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki et al., Bio/Technology 3 (1985), 1008-1012), allele-specific oligonucleotide (ASO) probe analysis (Conner et al., Proc. Natl. Acad. Sci. USA 80 (1983), 278), oligonucleotide ligation assays (OLAs) (Landegren et al., Science 241 (1988), 1077), and the like. Molecular techniques for DNA analysis have been reviewed (Landegren et al., Science 242 (1988), 229-237). Hence, the method of the present invention can also be used for transcriptional profiling of embryonic and adult stem cells; see, e.g., Ramalho-Santos et al., Science 298 (2002), 597-600; Tanaka et al., Genome Res. 12 (2002), 1921-1928.

Incubating includes conditions which allow contact between the test compound and the ES cells or ES-derived cells. Contacting can be done under both in vitro and in vivo conditions. For example, it may be desirable to test an array of compounds or small molecules on a single or few ES cells on a "chip" or other solid support; see supra. For example, cardiomyocytes or neurons on chips would give a readout of the rate of contraction or number of firings, respectively, in response to a compound and for the detection of harmful or at least biologically active environmental agents.

Neuronal biologically compatible electrode arrays allow the stem cells to undergo further differentiation on the array itself. These arrays allow the measurement of real time changes in electrical activity in the ES cell-derived neurons in response to the presence of known or unidentified agents. The electrical activity of cardiomyocytes can be monitored by plating the cells on an array of extracellular microelectrodes (Connolly et al., Biosens. Biores. 5 (1990), 223-234). The cells show regular contractions, and the extracellular signal recorded shows a relationship to intracellular voltage recordings (Connolly et al., supra). This non-invasive method allows long-term monitoring and is simpler and more robust than typical whole cell patch clamp techniques.

Hence, in a preferred method of the present invention, the phenotypic response to be determined comprises electrophysiological properties, preferably determined during the ongoing differentiation process. This embodiment is particularly suited to provide modulation reference patterns and databases of modulation reference patterns for a wide range of biologically active compounds. The reference patterns are then used for the identification and classification of test compounds. Evaluation of test compounds may be used to achieve different results.

Methods for the classification of biological agents according to the spectral density signature of evoked changes in cellular electric potential are known to the person skilled in the art; see, e.g., U.S. Pat. No. 6,377,057. Thus, biologically active compounds are classified according to their effect on ion channels, changes in membrane potential and ionic currents, and the frequency content of action potentials that the compound(s) evoke in excitable cells. The spectral density changes of such evoked membrane potential or action potential are a characteristic for each channel type that is modulated by the test compound. A pattern of spectral changes in membrane potential is determined by contacting a responsive cell with a compound, and monitoring the membrane potential or ionic currents over time. These changes correlate with the effect of that compound, or class of compounds, on the ion channels of the responding cell. This pattern of spectral changes provides a unique signature for the compound, and provides a useful method for characterization of channel modulating agents. The effect of a compound on ion channels, and on the action potential of a living cell, can provide useful information about the classification and identity of the compound. Methods and means for extracting such information are of particular interest for the analysis of biologically active compounds, with specific applications in pharmaceutical screening, drug discovery, environmental monitoring, biowarfare detection and classification, and the like. Examples of whole cell-based biosensors are described in Gross et al., Biosensors and Bioelectronics 10 (1995), 553-567; Hickman et al. Abstracts of Papers American Chemical Society 207 (1994), BTEC 76; and Israel et al., American Journal of Physiology: Heart and Circulatory Physiology 27 (1990), H1906-H1917. Connolly et al., Biosens. Biores. 5 (1990), 223-234, describe a planar array of microelectrodes developed for monitoring the electrical activity of cells in culture. The device allows the incorporation of surface-topographical features in an insulating layer above the electrodes. Semiconductor technology is employed for the fabrication of gold electrodes and for the deposition and patterning of an insulating layer of silicon nitride. The electrodes were tested using a cardiac cell culture of chick embryo myocytes, and the physical beating of the cultured cells correlated with the simultaneous extracellular voltage measurements obtained. The molecular control of cardiac ion channels is reviewed by Clapham, Heart Vessels Suppl. 12 (1997), 168-169. Oberg and Samuelsson, J. Electrocardiol. 14 (1981), 13942, performed fourier analysis on the repolarization phases of cardiac action potentials. Rasmussen et al., American Journal of Physiology 259 (1990), H370-H389, describe a mathematical model of electrophysiological activity in bullfrog atria.

A large body of literature exists in the general area of ion channels. A review of the literature may be found in the series of books, "The Ion Channel Factsbook", volumes 1-4, by Edward C. Conley and William J. Brammar, Academic Press. An overview is provided of: extracellular ligand-gated ion channels (ISBN: 0121844501), intracellular ligand-gated channels (ISBN: 012184451X), inward rectifier and intercellular channels (ISBN: 0121844528), and voltage-gated channels (ISBN: 0121844536). Hille, B. (1992) "Ionic Channels of Excitable Membranes", $2^{nd}$ Ed. Sunderland Mass.: Sinauer Associates.

In another aspect, cells cultured or modified using the materials and methods provided by the present invention are mounted to support surfaces to screen for bioactive substances. In one example, the cells are coupled with a substrate such that electrophysiological changes in the cells in response to external stimuli can be measured, e.g., for use as a high-throughput screen for bioactive substances. The cells can also be transfected with DNA that targets, expresses, or knocks-out specific genes or gene products in the cell. By providing such chip-mounted cells coupled with measuring devices, such as a computer, many compounds can be screened rapidly and accurately. The cells or chips could also be coupled to the measuring device in arrays for large-scale parallel screening.

The assay methods of the present invention can be in conventional laboratory format or adapted for high throughput. The term "high throughput" (HTS) refers to an assay design that allows easy analysis of multiple samples simultaneously, and has capacity for robotic manipulation. Another desired feature of high throughput assays is an assay design that is optimized to reduce reagent usage, or minimize the number of manipulations in order to achieve the analysis desired. Examples of assay formats include 96-well, 384-well or more-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

In the method of the invention, said cells are preferably contained in a container, for example in a well in a microtiter plate, which may be a 24-, 96-, 384- or 1586-well plate. Alternatively, the cells can be introduced into a microfluidics device, such as those provided by Caliper Newton, Mass., USA). In another preferred embodiment, the method of the present invention comprises taking 2, 3, 4, 5, 7, 10 or more measurements, optionally at different positions within the container. In one embodiment of the screening methods of the present invention a compound known to activate or inhibit differentiation process and/or tissue structure formation is added to the sample or culture medium, for example retinoic acid; for appropriate compounds see also supra.

Furthermore, the above-described methods can, of course, be combined with one or more steps of any one of the above-described screening methods or other screening methods well-known in the art. Methods for clinical compound discovery comprise for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization. Once a drug has been selected, the method can have the additional step of repeating the method used to perform rational drug design using the modified drug and to assess whether said modified drug displays better affinity according to for example interaction/energy analysis. The method of the present invention may be repeated one or more times such that the diversity of said collection of compounds is successively reduced.

Substances are metabolized after their in vivo administration in order to be eliminated either by excretion or by metabolism to one or more active or inactive metabolites (Meyer, J. Pharmacokinet. Biopharm. 24 (1996), 449-459). Thus, rather than using the actual compound or drug identified and obtained in accordance with the methods of the present invention, a corresponding formulation as a pro-drug can be used which is converted into its active form in the patient by his/her metabolism. Precautionary measures that may be taken for the application of pro-drugs and drugs are described in the literature; see, for review, Ozama, J. Toxicol. Sci. 21 (1996), 323-329.

Furthermore, the present invention relates to the use of a compound identified, isolated and/or produced by any one of these methods for the preparation of a composition for the treatment of disorders related to, for example, damaged tissue or aberrant tissue or organ formation, heart insufficiency, etc.; see also supra. Preferably, the isolated compound or corresponding drug supports wound healing and/or healing of damaged tissue. As a method for treatment the identified substance or the composition containing it can be administered to a subject suffering from such a disorder. Compounds identified, isolated and/or produced by the method described above can also be used as lead compounds in drug discovery and preparation of drugs or prodrugs. This usually involves modifying the lead compound or a derivative thereof or an isolated compound as described hereinbefore such as modifying said substance to alter, eliminate and/or derivatize a portion thereof suspected causing toxicity, increasing bioavailability, solubility and/or half-life. The method may further comprise mixing the substance isolated or modified with a pharmaceutically acceptable carrier. The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogs are-well known to those skilled in the art and are described in, for example, Beilstein, Handbook of Organic Chemistry, Springer Edition New York Inc., 175 Fifth Avenue, New York, N.Y. 10010 U.S.A., and Organic Synthesis, Wiley, New York, USA. Furthermore, peptidomimetics and/or computer-aided design of appropriate derivatives and analogues can be used, for example, according to the methods described above. Methods for the lead generation in drug discovery also include using proteins and detection methods such as mass spectrometry (Cheng et al., J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290), combinatorial biochemistry, classical chemistry and others (see, for example, Holzgrabe and Bechtold, Pharm. Acta Helv. 74 (2000), 149-155). Furthermore, examples of carriers and methods of formulation may be found in Remington's Pharmaceutical Sciences.

Once a drug has been selected in accordance with any one of the above-described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e., treatment, healing, prevention or amelioration of damaged tissue, or an increase in the rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response in a non-human animal test.

The present invention also relates to kit compositions containing specific reagents such as those described hereinbefore useful for conducting any one of the above-described methods of the present invention, containing the vector or the composition of vectors described hereinbefore, multi- or pluripotent cells, and optionally a culture medium, recombinant nucleic acid molecules, standard compounds, etc. Such a kit would typically comprise a compartmentalized carrier suitable to hold in close confinement at least one container. The carrier would further comprise reagents useful for performing said methods. The carrier may also contain a means for detection such as labeled enzyme substrates or the like.

Hence, the means and methods of the present invention described herein-before can be used in a variety of applications including, but not limited to "loss of function" assays with ES cells containing homozygous mutations of specific genes, "gain of function" assays with ES cells overexpressing exogenous genes, developmental analysis of teratogenic/embryotoxic compounds in vitro, pharmacological assays and the establishment of model systems for pathological cell functions, and application of differentiation and growth factors for induction of selectively differentiated cells which can be used as a source for tissue grafts; see for review, e.g., Guan et al., Altex 16 (1999), 135-141.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL), are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. A more complete understanding can be obtained by reference to the following specific examples and figures which are provided herein for purposes of illustration only and are not intended to limit the scope of the invention. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

The practice of the present invention will employ, unless otherwise indicated, conventional techniques of cell biology, cell culture, molecular biology, transgenic biology, microbiology, recombinant DNA, and immunology, which are within the skill of the art.

For further elaboration of general techniques concerning stem cell technology, the practitioner can refer to standard textbooks and reviews, for example Teratocarcinomas and embryonic stem cells: A practical approach (E. J. Robertson, ed., IRL Press Ltd. 1987); Guide to Techniques in Mouse Development (P. M. Wasserman et al., eds., Academic Press 1993); Embryonic Stem Cell Differentiation in Vitro (Wiles, Meth. Enzymol. 225 (1993), 900); Properties and uses of Embryonic Stem Cells: Prospects for Application to Human Biology and Gene Therapy (Rathjen et al., Reprod. Fertil. Dev. 10 (1998), 31). Differentiation of stem cells is reviewed in Robertson, Meth. Cell Biol. 75 (1997), 173; and Pedersen, Reprod. Fertil. Dev. 10 (1998), 31. Besides the sources for stem cells described already above further references are provided; see Evans and Kaufman, Nature 292 (1981), 154-156; Handyside et al., Roux's Arch. Dev. Biol., 196 (1987), 185-190; Flechon et al., J. Reprod. Fertil. Abstract Series 6 (1990), 25; Doetschman et al., Dev. Biol. 127 (1988), 224-227; Evans et al., Theriogenology 33 (1990), 125-128; Notarianni et al., J. Reprod. Fertil. Suppl., 43 (1991), 255-260; Giles et al., Biol. Reprod. 44 (Suppl. 1) (1991), 57; Strelchenko et al., Theriogenology 35 (1991), 274; Sukoyan et al., Mol. Reprod. Dev. 93 (1992), 418-431; Iannaccone et al., Dev. Biol. 163 (1994), 288-292.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (D. N. Glover ed., 1985); Oligonucleotide Synthesis (M. J. Gait ed., 1984); Nucleic Acid, Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Gene Transfer Vectors for Mammalian Cells (Miller & Calos, eds.); Current Protocols in Molecular Biology and Short Protocols in Molecular Biology, 3rd Edition (F. M. Ausubel et al., eds.); and Recombinant DNA Methodology (R. Wu ed., Academic Press). Gene Transfer Vectors For Mammalian Cells (J. H. Miller and M. P. Calos eds., 1987, Cold Spring Harbor Laboratory); Methods In Enzymology, vols. 154 and 155 (Wu et al. eds.); Immobilized Cells And Enzymes (IRL Press, 1986); B. Perbal, A Practical Guide To Molecular Cloning (1984); the treatise, Methods In Enzymology (Academic Press, Inc., N.Y.); Immunochemical Methods In Cell And Molecular Biology (Mayer and Walker eds., Academic Press, London, 1987); Handbook Of Experimental Immunology, Volumes I-IV (D. M. Weir and C. C. Blackwell eds., 1986). Reagents, cloning vectors, and kits for genetic manipulation referred to in this disclosure are available from commercial vendors such as BioRad, Stratagene, Invitrogen, and ClonTech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251). Other observations about the media and their impact on the culture environment have been made by Marshall McLuhan and Fred Allen.

EXAMPLES

Example 1

Generation of the Transgenic ES Cell Clones for Drug Selection of the ES Cell-Derived Cardiomyocytes Design of the Vector The 5.5 kb BamHI-SalI fragment of promoter region for cardiac-specific α-myosin heavy chain (αMHC) (GenBank accession No: U71441; Subramaniam et al., J. Biol. Chem. 266 (1991), 24613-24620; Sanbe et al., Circ. Res. 92 (2003), 609-616) and coding region for puromycin-resistant cassette (Pac) have been inserted consequently in the multicloning (MCS) site of the pIRES2-EGFP vector (Clontech®) after human cytomegalovirus (CMV) early promoter ($P_{CMV}$ IE) has been excised by AseI-Eco47 III. In resulting bicistronic vector (paPIG) cardiac-specific αMHC promoter drives expression of both Pac as a drug selective marker and enhanced green fluorescent protein (EGFP) as a live reporter gene. The IRES (internal ribosome entry site) sequence provides the separate translation of both proteins in stably transfected cells. The vector contains also the kanamycin- and neomycin-resistant cassettes for transfectants selection in the cultures of bacterial and ES cells, respectively.

Transfection and Selection of the ES Cell Clones $5 \times 10^6$ ES cells (line D3; Doetschman et al., J. Embryol. Exp. Morph. 87 (1985), 27-45) have been electroporated with 30 μg of DNA of the paPIG vector linearized by SacI. Cells have been seeded on the 10 cm tissue culture dish containing monolayer of the mitomycin-inactivated neomycin-resistant feeder cells. 48 hrs after seeding, neomycin (G418) 300 μg/ml has been added to the culture medium for selection of the stably transfected ES cell clones. 8 to 10 days after start of selection the colonies of surviving ES cells have been picked up, trypsinized, propagated consequently on 48 wells, 24 wells and 6 cm plates. Resulting clones have been used in cardiac differentiation protocol for screening.

The differentiation has been performed according to the standard "hanging drop" protocol as described in, e.g., Maltsev et al., Circ. Res. 75 (1994), 233-244. On day 8 to 10 of development the beating embryoid bodies (EBs) expressing EGFP fluorescence have been treated with puromycin 10 µg/ml. The cell death under puromycin has been evident already after 12 hrs of treatment when in the number of clones the beating clusters of EGFP-positive cells not only survived a treatment but also showed intensified beating rate. Already after 3 to 5 days of treatment intensely beating EGFP-positive cell clusters presented the main cell fraction in plated EBs as well as in the suspension culture of EBs.

Two clones (αPIG10 and αPIG44) which showed the cardiac specific expression of both EGFP and puromycin resistance cassettes have been selected and used for further experiments.

Example 2

Co-Cultivation of the Purified ES Cell-Derived Cardiac Cells and Mouse Embryonic Fibroblasts After 7 to 10 days of the puromycin treatment, the beating EGFP-positive clusters of cardiac cells have been collected by centrifugation, washed twice with PBS and treated with 0.1% of collagenase B (Boehringer, Mannheim) during 20 min at 37° C. After 10 min and at the end of incubation cell suspension has been gently pipetted through the blue tip of 1 ml pipette. Consequently, one, two and again two volumes of medium containing 20% of the fetal calf serum (FCS) have been added and cells were centrifugated and washed with this medium twice, resuspended and calculated under fluorescent microscope.

Figure 4:
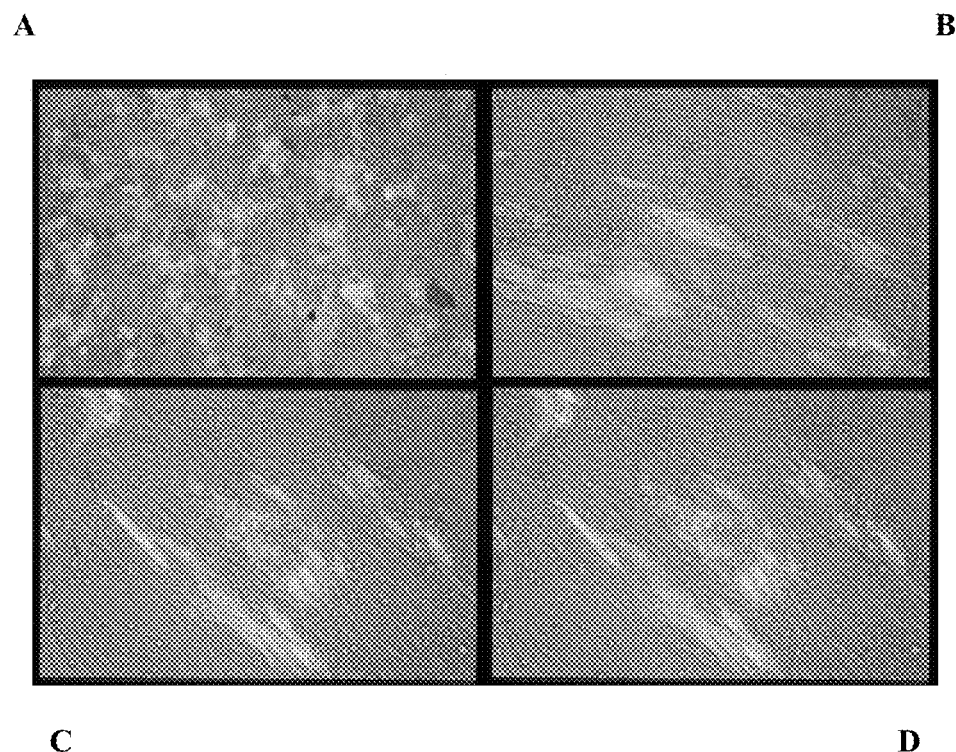
FIG. 4: ES cell-derived, puromycin-selected EGFP$^+$cardiomyocytes have been co-plated with mouse embryonic fibroblasts. A, B −1, 5 d; C and D −6 d in co-culture. Alignments of the EGFP+cardiomyocytes with fibroblasts on the 5th and 6th day, respectively, are evident.
Figure 5:
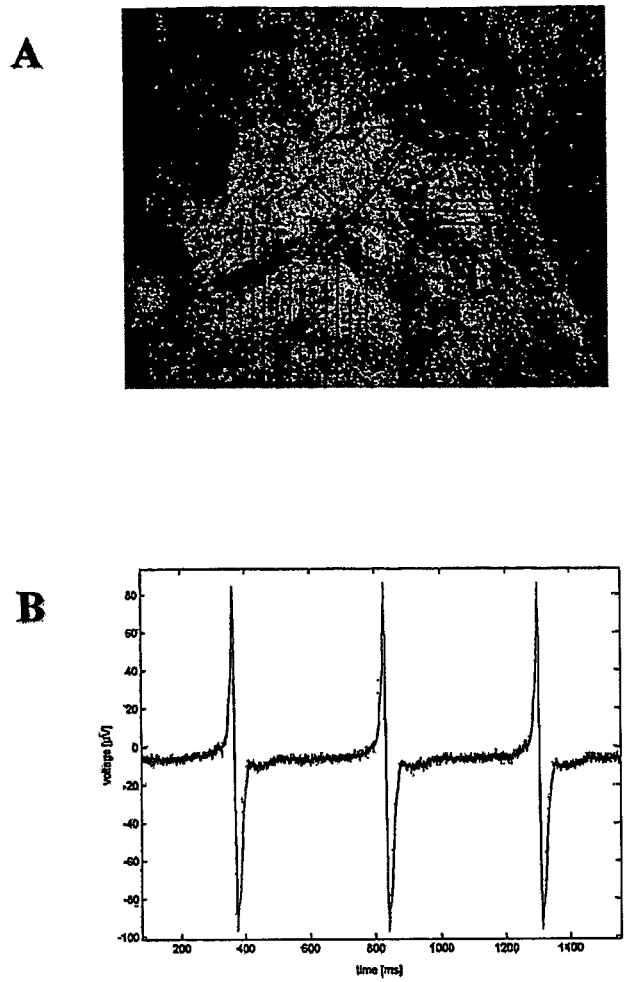
FIG. 5: Mouse embryonic fibroblasts and the puromycin-purified, EGFP-positive, ES cell-derived cardiomyocytes were dissociated by collagenase treatment and co-plated on the MEA. On day 4 after plating the beating EGFP-positive cardiac clusters were fully integrated into fibroblasts layer (A) and regular FP were recorded from most of them (B).

Mouse embryonic fibroblasts have been obtained from 14 to 16 d old embryos accordingly to standard procedure, see, e.g., Joyner A. L. Gene targeting. A Practical Approach. Oxford University Press, 1993. Cells were grown to the confluent and trypsinized with 0.05% trypsin, washed twice with medium containing 20% FCS and calculated. For co-cultivation approximately $50 \times 10^3$ to $100 \times 10^3$ fibroblasts were mixed with equal amount of the purified EGFP-positive ES cell-derived cardiomyocytes and plated on one well of the x24 well plate or, in some experiments, on Multi-Electrodes-Array (MEA). As shown in FIG. 4, one day after co-plating, fibroblasts formed monolayer whereas EGFP-positive cardiomyocytes showed only single or groups of cells slightly attached to fibroblasts. During the next few days ES cell-derived EGFP-positive cardiomyocytes showed complete integration and alignment with fibroblasts acquiring the longitudinal morphology and orientation in accordance with surrounding fibroblasts (FIG. 4). The cardiac cells integrated with embryonic fibroblasts showed viability and contractility during at least few weeks as has been shown in the MEA experiment (FIG. 5). For multi electrode array (MEA) assisted extracellular recording the ES cell-derived cardiomyocytes and fibroblasts were cultured on the multi electrode array (MEA; Multi Channel Systems, Reutlingen, Germany) consisting of a glass substrate (5 cm×5 cm) with 60 titanium nitride electrodes (30 µm diameter, 200 µm spacing) in the centre of the MEA and an internal reference electrode. Extracellular electrophysiological recordings from cardiomyocytes were performed with the MEA60 system (Multi Channel Systems, Reutlingen, Germany). The system comprises the MEA-1060 amplifier (bandwidth: 10 Hz to 3 kHz; amplification: 1200), the temperature controller HC-X to maintain 37° C. in the culture medium, and a computer system to record the measurement data with the MC_Rack software. The sample rate of the recordings was 4 kHz.

Example 3

Co-Transplantation of the Purified ES Cell-Derived Cardiac Cells and Mouse Embryonic Fibroblasts The mouse line SV129 has been used for preparation of embryonic fibroblasts by standard procedure (see, e.g., Joyner A. L. Gene targeting. A Practical Approach. Oxford University Press, 1993) in order to match the origin of the ES cell clones used for generation of cardiomyocytes. $50 \times 10^3$ to $100 \times 10^3$ of both purified cardiomyocytes and fibroblasts have been mixed and injected to the cryoinfarcted hearts of SV129 mice as described in Roell et al., Circulation 105 (2002), 2435-2441. The cardiomyocytes displaying both EGFP fluorescence and cross striation have been detected in transplanted hearts during the time frame of 10 to 70 days after operation (FIG. 6) thereby confirming viability of the engrafted ES cell derived cardiac cells.

Example 4

Principal Design of Transgenic ES Cell Clones for Tissue Modeling

Vector Design:

The basic elements for vectors are cell type-specific genomic regulatory elements (called further "promoters"), including common promoter and specific enhancer elements. Typically, they span the region upstream from the gene coding region and sometimes include also the untranslated intron-exon fragments. Promoters determine the cell-specific activation of the drug-resistant cassette that is the second basic element of vector and normally follows the promoter right downstream from the latter. Such combination allows eliminating non-differentiated ES cells along with cells differentiating towards irrelevant cell types from the cell type of interest that activates the drug-resistant cassette in the course of differentiation.

Additionally, it is recommended to include in the vector a so-called living color fluorescent protein cassette joined with the drug-resistant cassette via an internal ribosomal entry site (IRES). Such bicystronic vectors allow transcription of both drug-resistant and live reporter gene cassette from the same vector under one cell type-specific promoter. Later, the IRES permits independent ribosomal translation of both cassettes visualizing selected differentiated cells for monitoring. Up to date at least three color versions of enhanced green fluorescent protein (EGFP)—EYFP (yellow), ECFP (blue) and hcRFP (red)—are available for simultaneous visualizing of at least three different cell types in the same culture. The principal design of such vector is shown in FIG. 1.

Transgenic ES Clones:

The core of the method of the present invention is a parallel drug selection of cell types constituting tissue of interest in one culture of differentiating ES cells. The advantage of such approach is that interactions between purified cell types are processed in "natural" way immediately upon releasing from irrelevant cells, using natural cues for "cross-talk" signaling and forming viable tissue-like structure as an outcome. Two variants of such approach are presented:

a) multiple transgenic ES cell clones stably transfected with a certain number of vectors with drug selection cassettes driven by specific promoters according to the cell types constituting the desirable tissue type. In such a variant all emerging cell types have origin from one common ES cell clone predecessor and the resulting ratio between different cell components depends on the relative differentiation rate of each of them (FIGS. 2A and 3B);

b) chimeric embryoid bodies (EBs): by this approach a number of transgenic ES cell clones is generated where each single clone possesses only one vector with a drug-resistant cassette driven by one of the cell type-specific promoters. For tissue modeling the relevant clones should be mixed on initial phase of differentiation ("hanging drops" or "mass culture") in order to form ES cell aggregates (EBs) where, after drug selection, emerging cell types have origin from different corresponding ES cell clones and the final ratio of the cell components also depends on and can be controlled by initial ratio between different ES cell lines (FIGS. 2B and 3C).

Example 5

Cardiac Tissue Modeling in ES Cell System

A system for drug selection of the ES cell-derived cardiomyocytes based on the above-described principal scheme of the bicistronic vectors has been established. For this purpose, the cardiac-specific promoter for α-myosin heavy chain (αC-MHC promoter), and puromycin resistance cassette have been inserted as a "cell type-specific promoter" and "drug resistance cassette for cell type selection" (FIGS. 1 and 3A), respectively, in the vector pIRES2-EGFP (Clontech®) which possesses IRES, and enhanced green fluorescent protein (EGFP) as "IRES" and "live fluorescent reporter cassette" (FIG. 1), respectively; see also Examples 1 and 2 of international application WO02/051987. This system allows fast and efficient purification of the viable cardiomyocytes feasible for transplantation. The obvious advantages of this system are proven by the possibility of monitoring differentiation, cardiac specific selection and the fate of transplanted cells. It has also been shown that puromycin-purified cardiomyocytes completely integrate and align with embryonic fibroblasts during few days in co-culture (FIG. 4). In such co-culture ES cell-derived purified cardiomyocytes maintained a good functional state during at least two weeks when both spontaneous contraction and field potential (FA) signal were registered via multi electrode arrays (MEA) measurements (FIG. 5).

The fibroblasts are known as a key cell element of connective tissue in mammalian and non-mammalian species. Particularly in the mouse heart they constitute up to 50% in the embryonic and up to 80% in the adult heart. Another important non-cardiac element of the cardiac tissue is presented by endothelial cells as a main cell element for capillaries and vessels possessing an important trophic function. Thus, it is expected that ES cell-derived cardiac, endothelial and fibroblast cells can constitute a set sufficient to form cardiac-like tissue.

Vectors and ES Cell Clones Design:

1) For the cardiac-specific vector, the above-mentioned αMHC promoter can be used or other cardiac-specific promoters (MLC2v, MLC1a, MLC2a, β-MHC, etc) as "cell type-specific promoter" and enhanced cyan fluorescent protein (ECFP, Clontech®) as live reproter gene along with IRES and puromycin (or some other selective markers) cassettes in accordance with FIG. 3A.

2) For the endothelial-specific vector, Tie2 can be used (or other endothelial-specific promoters such as Tie1, Cadherin, etc) as "cell type-specific promoter", and enhanced yellow fluorescent protein (EYFP, Clontech®) as live reporter gene along with IRES and puromycin (or some other selective markers) cassettes in accordance with FIG. 3A.

3) For the fibroblast-specific vector collagen I can be used (or other fibroblast-specific promoters) as "cell type-specific promoter", and hcRed fluorescent protein (hcRFP, Clontech®) as live reporter gene along with IRES and puromycin (or some other selective markers) cassettes in accordance with FIG. 1.

ES cell clones design, differentiation and selection schemes can be performed in accordance with the above-described two main principles: "Three vectors—One clone" (FIG. 3B) or Three vectors—Three clones" (FIG. 3C). Transfection and selection of ES cell-derived cell types and transplantation is performed as described in international application WO02/051987 the disclosure content of which is incorporated herein by reference; see in particular Examples 1 and 2 of WO02/051987 and the references cited therein.

The use of three different live fluorescent reporter vectors allows to trace differentiation, selection and cell-to cell connections during tissue formation in one culture in the "live" mode. In vitro formation of the cardiac tissue-like structure in ES cell culture can be used as relevant, physiplogical system for testing of different cardiotropic and cardiotoxic substances in biochemical and electrophysiological (MEA) experiments. Furthermore, it could become a relevant source of transplanted material in the cardiac diseases replacement therapy.

Example 6

Double Transgenic System for Cardiovascular Selection in ES Cell System

The main goal of this experiment was a parallel selection of the two ES cell-derived cell types closely related to each other both functionally and by common mesodermal origin. For this purpose, stable double transgenic ES cell clones were generated, where one vector possesses a drug resistance cassette under the control of the cardiac-specific promoter whereas the second possesses both a drug resistance and a live fluorescence reporter cassette under the control of the endothelial-specific promoter. Cardiac and endothelial cells appear very early in the real embryonic development and constitute functionally and anatomically very closely related elements of the forming heart. Therefore, it was expected that being effectively selected from one culture of the differentiating ES cells, these cell types have to show patterns of a self-assembling driven by cues similar to ones taking place during a real embryonic cardiogenesis. In the first experimental version the endothelial-like cells had to be identified by enhanced green fluorescent protein (EGFP) fluorescence whereas the colorless cardiomyocyte-like cells by detection of the contractile clusters. In further experiments chimeric embryoid bodies were generated consisting of both the above-mentioned clone and another transgenic clone possessing red fluorescent protein (HcRFP) and a drug-resistant cassette both driven by a cardiac-specific promoter. Thus, the latter experiment allowed to visualize differentiation and selection of both cardiac and endothelial cell types.

Vectors:

1) For vector paMHC-Pac the puromycin resistance cassette (Pac) was excised from the pCre-Pac vector (Taniguchi et al., Nucleic Acid Research 26 (1998, 679-680) by Hind III-Sal I restriction enzymes and blunt-end ligated into the αMHC-EGFP vector after deletion of the EGFP cassette by BamH I-Afl II enzymes.

For electroporation of the ES cells, Hind III linearized resulting vector was used.

2) For vector pTie2-Pac-IRES-EGFP (pTie2-PIG) the Pac-IRES-EGFP cassette was excised from the pPIG vector by Sal I-Afl II and inserted by blunt ligation into Not I site of the pSPTg.T2FXK vector (Schlaeger et al., Proc. Natl. Acad. Sci. USA 94 (1997), 3058-3063) between Tie2 promoter and Tie2 enhancer.

For electroporation of ES cells, the Tie2 promoter-PIG-Tie2 enhancer fragment was excised from resulting vector by Sal I and purified by electrophoresis in the 1% agarose gel.

3) For vector p α MHC-hcRFP the 5.5 kb cardiac αMHC promoter fragment was excised by BamH I-Sal I from pαMHC-BS2SK (Robbins, Trends Cardiovasc. Med. 7 (1997), 185-191) and blunt-end ligated into the SmaI site of the pHcRed 1-1 (Clontech®, USA).

ES Cell Culture, Transformation and Differentiation Protocols:

ES cells were cultivated and electroporation performed as described (Kolossov et al., J. Cell Biol. 143 (1998), 2045-2056). $5 \times 10^6$ ES cells (D3 line) were co-transfected with 30 µg DNA of each paMHC-Pac and Tie2 promoter-PIG-Tie2 enhancer fragments. The G418-resistant clones were selected, propagated and underwent to differentiation as described (Kolossov et al., J. Cell Biol. 143 (1998), 2045-2056). For generation of the chimeric EBs, suspensions of the cells from transgenic clones Tie2-PIG/αMHC-Pac and αMHC-hcRFP/αMHC-Pac were mixed up to a cell density of $0.01 \times 10^6$ cells of each clone per 1 ml (200 cells of each clone per drop).

EBs was monitored via fluorescent microscope Axiovert 200M (Zeiss, Germany).

Clone Tie2-PIG/αMHC-Pac:

The spontaneous contractions started on day 8 to 10 of development. On day 11 to 14 the first EGFP-positive cells were detected exclusively in the beating EBs in the areas overlapping with or very close to the contractile cardiac clusters. At this time, puromycin (5 µg/ml) was added and then the medium was changed every 2-3 days. During the next days the increasing contractility of the cardiac clusters along with increasing EGFP expression were detected. At the same time, the intensive death of the puromycin non-resistant cells was registered. Typically, already after 4 days of the puromycin treatment the EGFP-positive cells formed a network embedded into vigorously beating clusters of cardiac cells. After 10 and more days of the puromycin treatment, the fluorescence intensity increased dramatically.

Chimeric EBs: Clone Tie2-PIG/αMHC-Pac+Clone αMHC-hcRFP/αMHC-Pac:

Like EBs from the above-described clone the chimeric EBs have shown the same time course of EGFP expression in the beating areas. Simultaneously, an intense RFP fluorescence was detected in the same beating areas thereby marking differentiated cardiomyocytes. Remarkably, EGFP and RFP fluorescent clusters were spatially overlapping but not completely superposed as beating clusters presented a clear green-red mosaic structure. Both green and red fluorescence increased significantly during puromycin treatment.

Thus, the above mentioned experiments unequivocally show a clear and strong connection between cardiac and endothelial differentiation in the ES cell system: EBs without contractile activity did not express any EGFP fluorescence too. Both cell types displayed also a high spatial accordance as most areas with EGFP-expressing cells were either localized very close to the beating clusters or completely overlapped with them. After puromycin treatment the connections between these two cell types became obvious: after death of most of the undifferentiated cells the networks of the EGFP fluorescent cells were embedded in the beating cardiac clusters frequently displaying signs of structural orientation. Remarkably, the intensity of the EGFP fluorescence was increased dramatically during puromycin treatment hinting on the proliferation of endothelial cells after release from undifferentiated ES cells as has been proven in accordance with the present invention for cardiac cells.

The tight connections between cardiac and endothelial elements particularly evident on the multi-colored fluorescent images of beating clusters allow to consider these structures as a possible proto-type of cardiovascular tissue-like structure created by means of the drug selection from differentiating multi transgenic ES cell culture.

Finally, the presented data point out on the principal feasibility of the "tissue modeling" via multi lineage selection in multi-transgenic ES cell system.

It will be recognized that the compositions and procedures provided in the description can be effectively modified by those skilled in the art without departing from the spirit of the invention embodied in the claims that follow.

The invention claimed is:

1. A method of modeling or producing a cardiac tissue comprising:
   (a) obtaining cardiomyocytes, wherein a first population of pluripotent cells is differentiated into said cardiomyocytes, wherein said differentiation includes forming embryoid bodies and isolating cardiomyocytes from said embryoid bodies;
   (b) obtaining fibroblasts, wherein a second population of pluripotent cells is differentiated into said fibroblasts;
   (c) co-culturing the cardiomyocytes obtained in step (a) with the fibroblasts obtained in step (b);
   (d) allowing integration and alignment of the cardiomyocytes and fibroblasts into a viable cardiac tissue;
   wherein the cardiomyocytes acquire longitudinal morphology upon integration and alignment with the fibroblasts; and
   wherein said viable cardiac tissue exhibits contractions for at least 2 weeks.

2. The method of claim 1, wherein the first population of pluripotent cells comprises a selectable marker gene operably linked to a cardiomyocyte-specific regulatory sequence.

3. The method of claim 1, wherein said selectable marker gene confers resistance to puromycin.

4. The method of claim 1, wherein the first population of pluripotent cells comprises a reporter gene operably linked to a cardiomyocyte-specific regulatory sequence.

5. The method of claim 4, wherein the first population of pluripotent cells further comprises a selectable marker gene operably linked to a cardiomyocyte-specific regulatory sequence, and wherein said cardiomyocyte-specific regulator sequence operably linked to the reporter gene is the same as said cardiomyocytes-specific regulatory sequence operably linked to the selective marker gene.

6. The method of claim 5, wherein said reporter gene is selected from different color versions of enhanced green fluorescent protein (EGFP).

7. The method of claim 5, wherein said marker gene and said reporter gene are contained in the same recombinant nucleic acid molecule.

8. The method of claim 7, wherein said marker gene and said reporter gene are contained in the same cistron.

9. The method of claim 2, wherein said cardiomyocyte-specific regulatory sequence is an atrial-specific regulatory sequence, ventricular specific regulatory sequence, or both an atrial and ventricular-specific regulatory sequence.

10. The method of claim 8, wherein said regulatory sequence is a promoter sequence and wherein said promoter sequence is an αMHC or MLC2V promoter sequence.

11. The method of claim 1, further comprising analyzing the physiological or developmental status or both of the cardiomyocytes and fibroblasts.

12. The method of claim 11, wherein the status is analyzed by monitoring the differentiation of electrical activity of the cardiomyocytes and fibroblasts on an array.

13. The method of claim 12, wherein said status is analyzed by recording the extracellular field potentials with a microelectrode array (MEA).

14. The method of claim 1, wherein said first and/or second population of pluripotent cells is genetically engineered to overexpress or inhibit the expression of a target gene.

15. The method of claim 1, wherein the cardiac tissue is produced and contained in a container.

16. The method of claim 15, comprising taking three or more measurements, optionally at different positions within the container.

17. The method of claim 15, wherein said container is a well in a microtiter plate.

18. The method of claim 17, wherein said microtiter plate is a 24-, 96-, 384- or 1586-well plate.

19. The method of claim 1, further comprising culturing the cardiomyocytes and fibroblasts in the presence of endothelial cells.

20. The method of claim 19, further comprising analyzing the physiological and/or developmental status of the cardiomyocytes, fibroblasts, and endothelial cells.

21. The method of claim 20, wherein the status is analyzed by monitoring the differentiation of electrical activity of the cardiomyocytes, fibroblasts, and endothelial cells on an array.

* * * * *